(12) United States Patent
Gooβen et al.

(10) Patent No.: US 8,372,972 B2
(45) Date of Patent: Feb. 12, 2013

(54) PROCESS FOR THE PREPARATION OF DIHYDROQUINAZOLINES

(75) Inventors: Käthe Gooβen, Kaiserslautern (DE);
Oliver Kuhn, Luxembourg (DE);
Mathias Berwe, Sprockhoevel (DE);
Joachim Kruger, Duesseldorf (DE);
Hans-Christian Militzer, Bergisch Gladbach (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 13/308,418

(22) Filed: Nov. 30, 2011

(65) Prior Publication Data

US 2012/0130072 A1 May 24, 2012

Related U.S. Application Data

(62) Division of application No. 11/922,280, filed as application No. PCT/EP2006/005298 on Jun. 2, 2006, now Pat. No. 8,084,604.

(30) Foreign Application Priority Data

Jun. 15, 2005 (DE) .......................... 10 2005 027 517

(51) Int. Cl.
C07D 239/72 (2006.01)
(52) U.S. Cl. ...................................... 544/283
(58) Field of Classification Search .................... 544/283
See application file for complete search history.

(56) References Cited

U.S. PATENT DOCUMENTS

| | | | |
|---|---|---|---|
| 5,854,245 | A | 12/1998 | Duggan et al. |
| 7,196,086 | B2 | 3/2007 | Wunberg et al. |
| 7,271,260 | B2 | 9/2007 | Lee et al. |
| 2002/0019397 | A1 | 2/2002 | Schnute et al. |
| 2003/0216401 | A1 | 11/2003 | Bentley et al. |
| 2005/0065160 | A1 | 3/2005 | Wunberg et al. |
| 2006/0211683 | A1 | 9/2006 | Selliah et al. |
| 2006/0235032 | A1 | 10/2006 | Wunberg et al. |
| 2007/0066622 | A1 | 3/2007 | Wunberg et al. |
| 2007/0185121 | A1 | 8/2007 | Wunberg et al. |
| 2007/0281953 | A1 | 12/2007 | Wunberg et al. |
| 2008/0132515 | A1 | 6/2008 | Wunberg et al. |
| 2009/0221822 | A1 | 9/2009 | Goossen et al. |
| 2010/0179174 | A1 | 7/2010 | Wunberg et al. |
| 2010/0280021 | A1 | 11/2010 | Berthel et al. |

FOREIGN PATENT DOCUMENTS

| | | |
|---|---|---|
| EP | 1 201 765 | 5/2002 |
| WO | WO-99/41253 | 8/1999 |
| WO | WO-2004/041790 | 5/2004 |
| WO | WO-2004/072048 | 8/2004 |
| WO | WO-2004/096778 | 11/2004 |
| WO | WO-2004/099212 | 11/2004 |

OTHER PUBLICATIONS

Desai et al., Indian J. Exp. Biol. (1998) 36(12):1280-1283 (abstract).
Desai et al., Farmaco (1996) 51(5):361-366 (abstract).
Gribaudo et al., Virus Research (2001) 73:57-65.
Griesser, Chapter 8, The Importance of Solvates (pp. 211-230), in the text, Polymorphism: In the Pharmaceutical Industry, Hilfiker, 2006.
Lee et al., Bioorganic & Medicinal Chemistry Letters (2004) 14:3379-3384.
Lischka et al., Current Opinion in Pharmacology (Article in Press, Corrected Proof) (2008) 8:1-8.
Martinez et al., Antiviral Chem. Chemo. (2003) 14:107-114.
Molina et al., Synthesis (1998) 3:283-287.
Saito et al., Tet. Letts. (1996) 37(2):209-212.
Search Report from Ecuadorian Patent Application No. SP 05-6138, 1 page.
Vippagunta et al., Advanced Drug Delivery Review (2001) 48:3-26.
Viral Defense Found., http://www.viraldefense.org/mission.htm, downloaded Oct. 21, 2008.
Visiting Nurse Assns. of America, http://www.vnaa.org/vnaa/gen/Germ_Protection_Center_Cold_and_Flu_Resources, downloaded Oct. 21, 2008.
Wang et al., Tet. Letts. (1997) 38(50):8651-8654.
Wikipedia, Maribavir, updated Feb. 10, 2009, http://en.wikipedia.org/wiki/Maribavir, downloaded Mar. 10, 2009.
Wilson et al., Med. Chem. Res. (1992) 2:102-110 (abstract).
Xin et al., Tetrahedron Letters (2000) 41(8):1147-1150.

*Primary Examiner* — Brian McDowell
(74) *Attorney, Agent, or Firm* — Morrison & Foerster LLP

(57) ABSTRACT

The present invention relates to a process for the preparation of dihydroquinazolines, for example, methyl (S)-{8-fluoro-2-[4-(3-methoxyphenyl)piperazin-1-yl]-3-[2-methoxy-5-(trifluoro-methyl)-phenyl]-3,4-dihydroquinazolin-4-yl}acetate (2S,3S)-2,3-bis[(4-methylbenzoyl)-oxy]succinic acid salt, which are used for the production of antiviral medicaments.

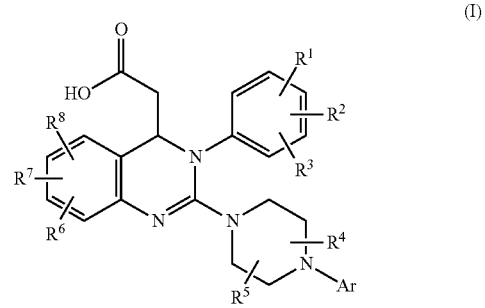

(I)

2 Claims, No Drawings

PROCESS FOR THE PREPARATION OF DIHYDROQUINAZOLINES

CROSS-REFERENCE TO RELATED APPLICATIONS

This application is a divisional of U.S. application Ser. No. 11/922,280, filed on Apr. 13, 2009, now U.S. Pat. No. 8,084,604, which is a National Phase Application of International Application No. PCT/EP2006/005298, filed Jun. 2, 2006, which claims the benefit of German Application No. 102005027517.6 filed on Jun. 15, 2005, the entire contents of each of which are incorporated herein by reference in their entirety.

The present invention relates to a process for the preparation of dihydroquinazolines, which are used for the production of medicaments.

The compounds prepared by the process according to the invention are suitable for use as antiviral agents, in particular against cytomegaloviruses, such as described in WO 04/072048 and WO 04/096778.

The synthesis of the dihydroquinazolines described there is carried out starting from a 2-halogeno-substituted aniline (A), which is converted by means of Heck coupling to a 2-aminocinnamic acid derivative (B). By reaction with triphenylphosphine in carbon tetrachloride, a phosphine imide (C) is prepared, which is subsequently reacted with an isocyanate with release of triphenylphosphine oxide to give a carbodiimide (D). By reaction of the carbodiimide (D) with an amine, the dihydroquinazoline methyl ester (E) results, which is separated into the enantiomers by chromatography on a chiral phase. Subsequently, hydrolysis to the dihydroquinazoline acid (F1) is carried out under standard conditions. The following schemes 1 and 2 illustrate the synthesis.

Scheme 1:

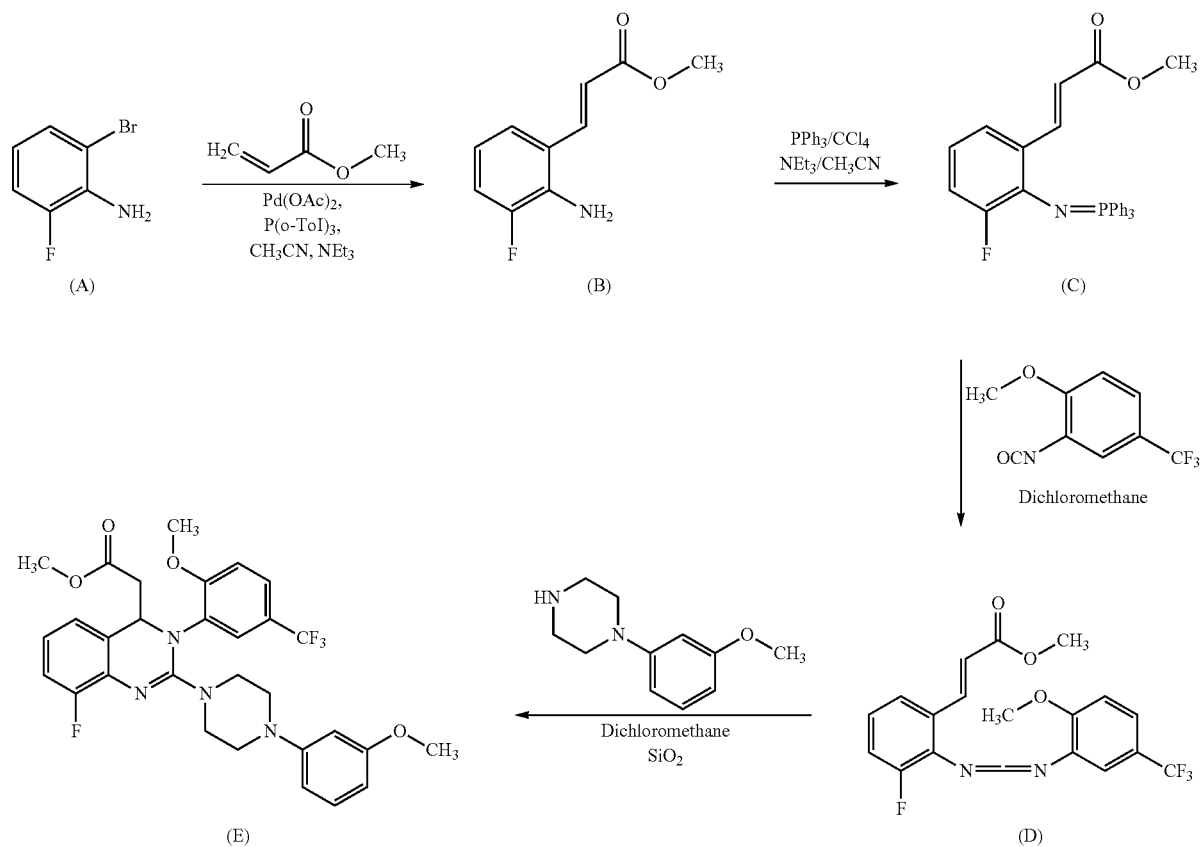

Scheme 2:

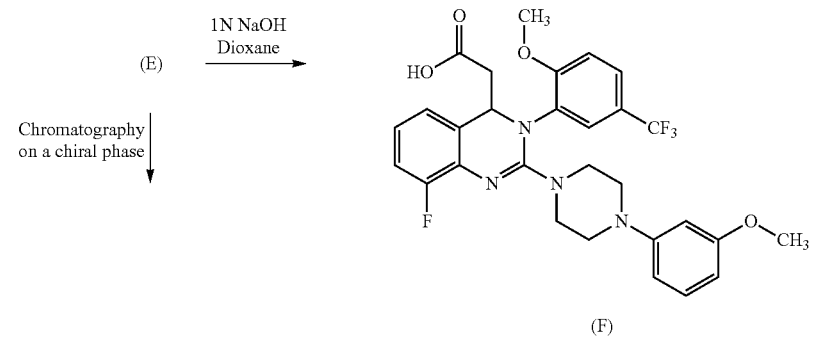

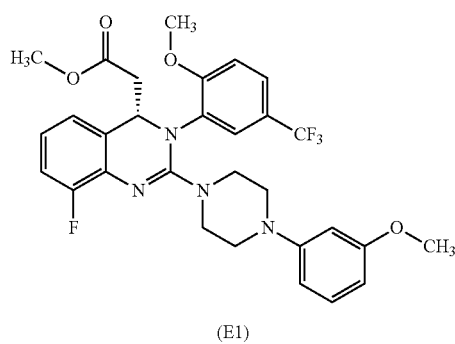
(E1)

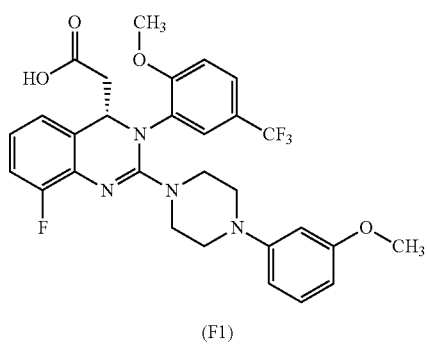
(F1)

The reaction steps described above involve distinct risks when carrying out on the industrial scale, and by-products and also stoichiometric amounts of organic waste products result. Using the phosphine imide (C) and the carbodiimide (D), intermediates having highly reactive functionalities result during the reaction sequence, which lead to by-products to a considerable extent. The by-products can only be separated by very laborious chromatographic purification or by a laborious extraction process.

Furthermore, during the reaction of the compound of the formula (C) to give the compound of the formula (D), triphenylphosphine oxide results in stoichiometric amounts, which is separated off from the desired product chromatographically in a laborious process. Chromatography in the synthesis of compounds on the industrial scale is particularly disadvantageous, since it is time-consuming and labour-intensive and consumes relatively large amounts of solvent.

The separation of the enantiomers of the compound of the formula (E) is carried out in a laborious process by chromatography on a chiral phase, the undesired R enantiomer being formed as a waste product.

It is the object of the present invention to make available an industrially applicable process for the preparation of a dihydroquinazoline of the formula (I), in particular of (S)-{8-fluoro-2-[4-(3-methoxyphenyl)piperazin-1-yl]-3-(2-methoxy-5-trifluoromethylphenyl)-3,4-dihydroquinazolin-4-yl}acetic acid, in which the disadvantages of the above process steps known from the prior art are avoided, and in which no undesired R enantiomer is formed as a waste product.

This object is achieved as follows according to the present invention. The following schemes 3 and 4 illustrate the individual reaction steps.

Scheme 3:

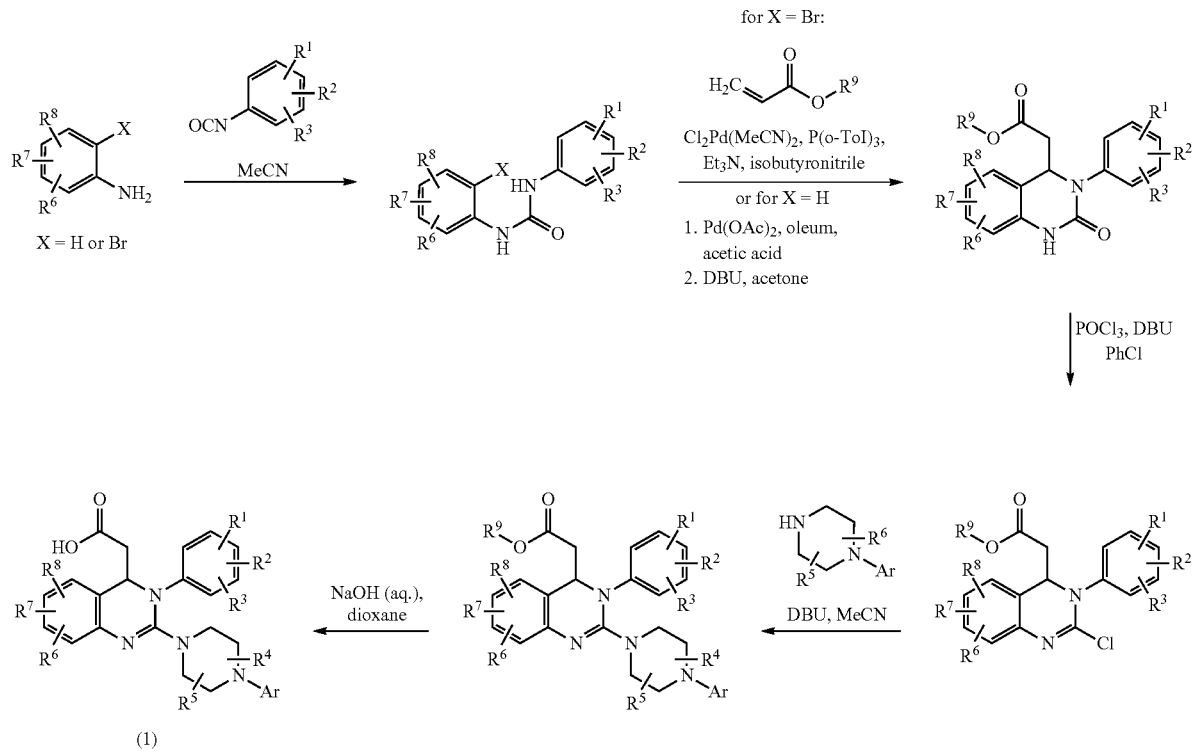

Scheme 4:
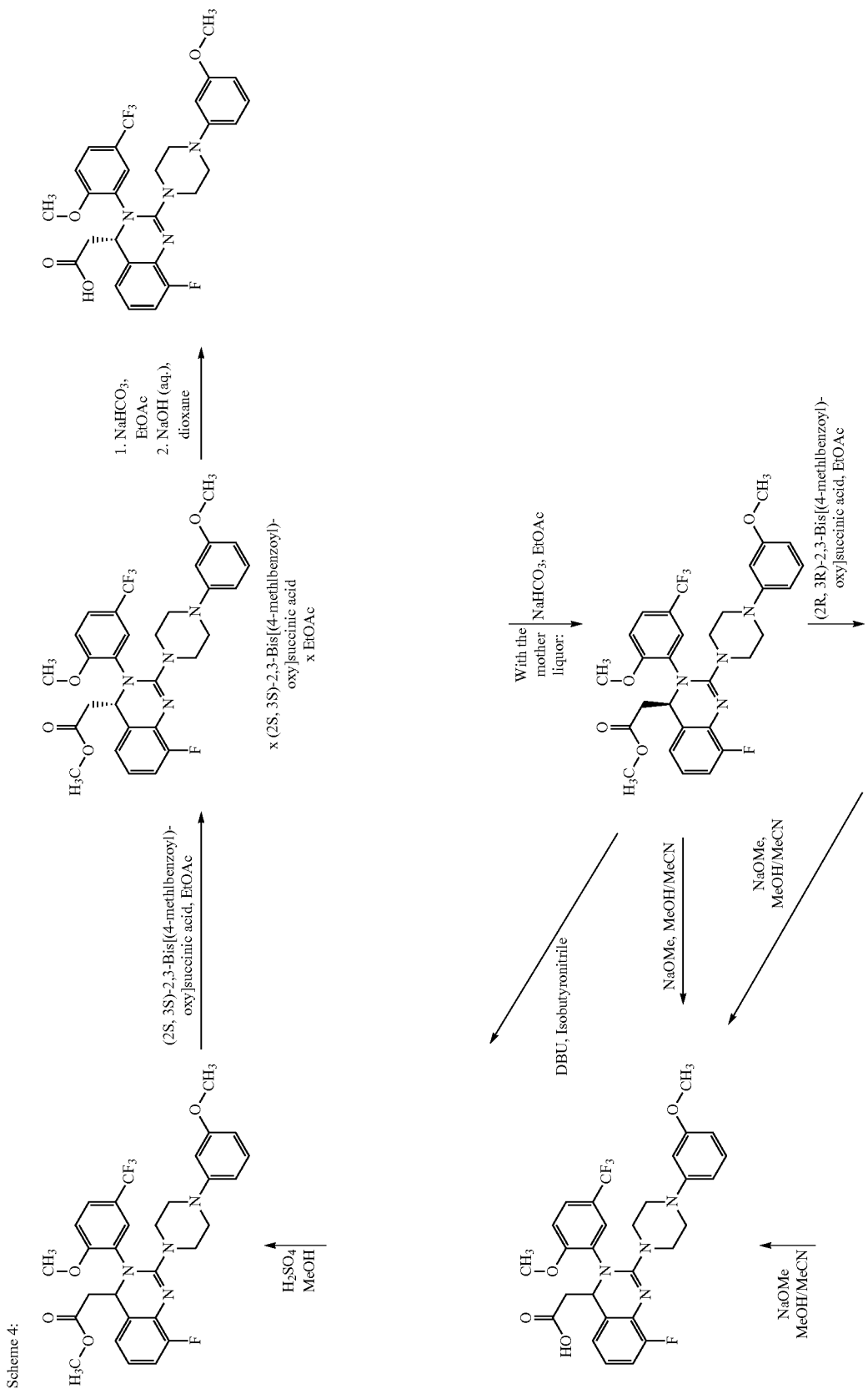

-continued
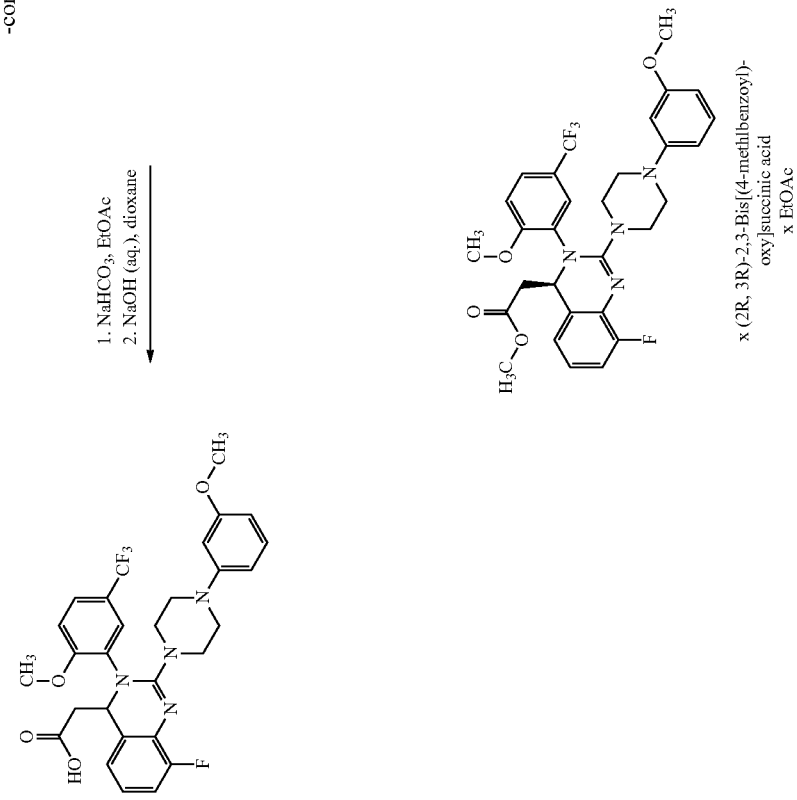

Surprisingly, it has now been found that compounds of the formula (I) can be prepared by the process according to the invention, i.e. by reaction of the 2-halogeno-substituted aniline with an isocyanate and a subsequent Heck reaction with alkyl acrylate, preferably methyl acrylate, and that a phosphine imide and a carbodiimide as reactive intermediates or the formation of stoichiometric amounts of triphenylphosphine oxide can thus be avoided.

In addition, it has surprisingly been found that the compounds of the intermediate stages form crystals and can be purified by crystallization without chromatography or extraction, whereby the industrial application of these process stages is made possible.

In addition, it has surprisingly been found that the structural unit methyl {8-fluoro-3-[2-methoxy-5-(trifluoromethyl)phenyl]-2-oxo-1,2,3,4-tetrahydroquinazolin-4-yl}acetate can be synthesized efficiently by means of an ortho-palladization. Here, N-(2-fluorophenyl)-N'-[2-methoxy-5-(trifluoromethyl)phenyl]urea is reacted with methyl acrylate and an oxidizing agent in the presence of an acid to give methyl (2E)-3-{3-fluoro-2-[({[2-methoxy-5-(trifluoromethyl)phenyl]amino}-carbonyl)amino]phenyl}acrylate. The ring closure to the tetrahydroquinazoline then follows under basic reaction conditions.

In addition, it has surprisingly been found that the alkyl {8-fluoro-2-[4-(3-methoxyphenyl)piperazin-1-yl]-3-[2-methoxy-5-(trifluoromethyl)phenyl]-3,4-dihydroquinazolin-4-yl}acetate, preferably the methyl {8-fluoro-2-[4-(3-methoxyphenyl)piperazin-1-yl]-3-[2-methoxy-5-(trifluoromethyl)phenyl]-3,4-dihydroquinazolin-4-yl}acetate, can be separated into the enantiomers by crystallization with (2S,3S)-2,3-bis[(4-methylbenzoyl)oxy]succinic acid.

In addition, it has surprisingly been found that the R enantiomer of alkyl {8-fluoro-2-[4-(3-methoxyphenyl)piperazin-1-yl]-3-[2-methoxy-5-(trifluoromethyl)phenyl]-3,4-dihydroquinazolin-4-yl}acetate, preferably of methyl {8-fluoro-2-[4-(3-methoxyphenyl)piperazin-1-yl]-3-[2-methoxy-5-(trifluormethyl)phenyl]-3,4-dihydroquinazolin-4-yl}acetate, can be racemized under basic conditions after the hydrolysis of the alkyl or methyl ester to the stage of the acid and can be separated after fresh esterification by crystallization with (2S,3S)-2,3-bis[(4-methylbenzoyl)-oxy]succinic acid, whereby the total yield of S enantiomer is increased.

In detail, the process according to the invention for the preparation of a compound of the formula (I)

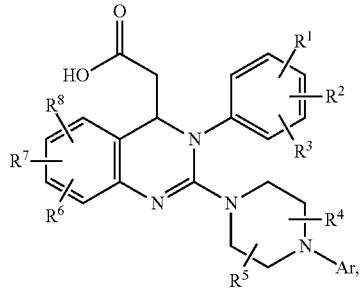

in which
Ar represents aryl, in which aryl can be substituted by 1 to 3 substituents, where the substituents independently of one another are selected from the group consisting of alkyl, alkoxy, formyl, carboxyl, alkylcarbonyl, alkoxycarbonyl, trifluoromethyl, halogen, cyano, hydroxyl, amino, alkylamino, aminocarbonyl and nitro,
  in which alkyl can be substituted by 1 to 3 substituents, where the substituents independently of one another are selected from the group consisting of halogen, amino, alkylamino, hydroxyl and aryl,
  or two of the substituents on the aryl, together with the carbon atoms to which they are bonded, form a 1,3-dioxolane, a cyclopentane ring or a cyclohexane ring and an optionally present third substituent independently thereof is selected from the group mentioned,
$R^1$ represents hydrogen, amino, alkyl, alkoxy, alkylamino, alkylthio, cyano, halogen, nitro or trifluoromethyl,
$R^2$ represents hydrogen, alkyl, alkoxy, alkylthio, cyano, halogen, nitro or trifluoromethyl,
$R^3$ represents amino, alkyl, alkoxy, alkylamino, alkylthio, cyano, halogen, nitro, trifluoromethyl, alkylsulphonyl or allylaminosulphonyl
or
one of the radicals $R^1$, $R^2$ and $R^3$ represents hydrogen, alkyl, alkoxy, cyano, halogen, nitro or trifluoromethyl and the other two, together with the carbons to which they are bonded, form a 1,3-dioxolane, a cyclopentane ring or a cyclohexane ring,
$R^4$ represents hydrogen or alkyl,
$R^5$ represents hydrogen or alkyl
or
the radicals $R^4$ and $R^5$ in the piperazine ring are bonded to exactly opposite carbon atoms and form a methylene bridge optionally substituted by 1 or 2 methyl groups,
$R^6$ represents hydrogen, alkyl, alkoxy, alkylthio, formyl, carboxyl, aminocarbonyl, alkylcarbonyl, alkoxycarbonyl, trifluoromethyl, halogen, cyano, hydroxyl or nitro,
$R^7$ represents hydrogen, alkyl, alkoxy, alkylthio, formyl, carboxyl, alkylcarbonyl, alkoxy-carbonyl, trifluoromethyl, halogen, cyano, hydroxyl or nitro
and
$R^8$ represents hydrogen, alkyl, alkoxy, alkylthio, formyl, carboxyl, alkylcarbonyl, alkoxy-carbonyl, trifluoromethyl, halogen, cyano, hydroxyl or nitro,
comprises the hydrolysis of the ester of a compound of the formula (II)

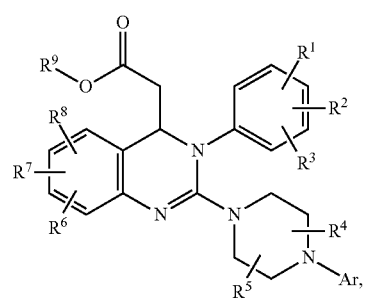

in which
Ar, $R^1$, $R^2$, $R^3$, $R^4$, $R^5$, $R^6$, $R^7$ and $R^8$ have the meaning indicated above, and
$R^9$ represents $C_1$-$C_4$-alkyl,
with a base or an acid.

The compound of the formula (II) can be prepared by reaction of a compound of the formula (III)

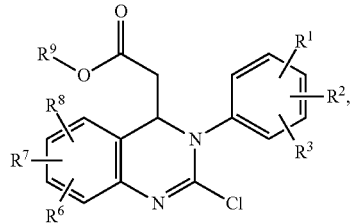

(III)

in which
$R^1, R^2, R^3, R^6, R^7$ and $R^8$ have the meaning indicated above, and
$R^9$ represents $C_1$-$C_4$-alkyl,
in the presence of a base
with a compound of the formula (IV)

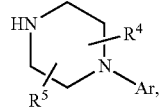

(IV)

in which
Ar, $R^4$ and $R^5$ have the meaning indicated above.

The compound of the formula (III) can be prepared by reaction of a compound of the formula (V)

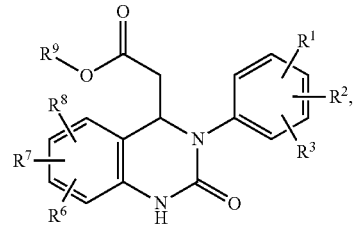

(V)

in which
$R^1, R^2, R^3, R^6, R^7$ and $R^8$ have the meaning indicated above, and
$R^9$ represents $C_1$-$C_4$-alkyl,
with phosphorus oxychloride, phosphorus trichloride or phosphorus pentachloride in the presence of a base.

The compound of the formula (V) can be prepared by reaction of a compound of the formula (VI)

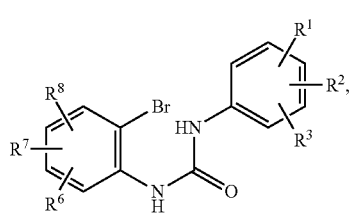

(VI)

in which
$R^1, R^2, R^3, R^6, R^7$ and $R^8$ have the meaning indicated above,
with a compound of the formula

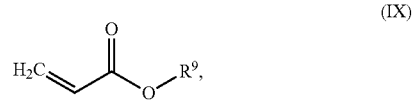

(IX)

in which
$R^9$ represents $C_1$-$C_4$-alkyl,
in the presence of a palladium catalyst and a base.

Compounds of the formulae (IV), (VI) and (IX) known per se to the person skilled in the art or can be prepared by customary processes known from the literature.

In an alternative process, a compound of the formula (V) can be prepared by reacting a compound of the formula (VII)

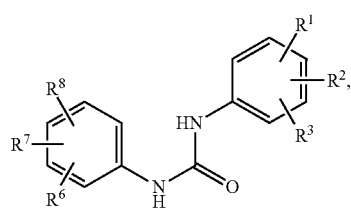

(VII)

in which
$R^1, R^2, R^3, R^6, R^7$ and $R^8$ have the meaning indicated above,
in the first stage with a compound of the formula (IX) in acetic acid in the presence of a palladium catalyst, an oxidizing agent and an acid to give a compound of the formula (VIII)

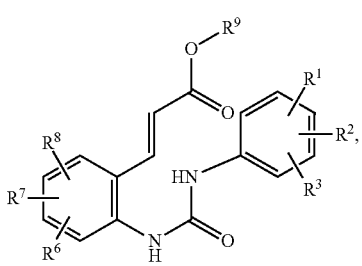

(VIII)

in which
$R^1, R^2, R^3, R^6, R^7$ and $R^8$ have the meaning indicated above, and
$R^9$ represents $C_1$-$C_4$-alkyl,
and in the second stage reacting with a base to give a compound of the formula (V).

Compounds of the formula (VII) are known per se to the person skilled in the art or can be prepared by customary processes known from the literature.

According to a preferred embodiment of the present invention, in the synthesis process the radical $R^9$ in the compounds of the formulae (II), (BI), (V), (VIII) and (IX) represents methyl.

In addition, the present invention comprises compounds of the formula (III)

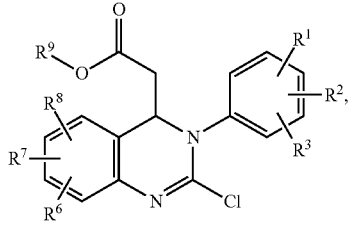

(III)

in which
R$^1$, R$^2$, R$^3$, R$^6$, R$^7$ and R$^8$ have the meaning indicated above, and
R$^9$ represents C$_1$-C$_4$-alkyl.

Compounds of the formula (III) are preferred in which R$^9$ represents methyl.

In addition, the present invention comprises compounds of the formula (V)

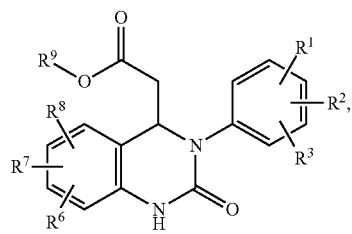

(V)

in which
R$^1$, R$^2$, R$^3$, R$^6$, R$^7$ and R$^8$ have the meaning indicated above, and
R$^9$ represents C$_1$-C$_4$-alkyl.

Compounds of the formula (V) are preferred in which R$^9$ represents methyl.

According to a particularly preferred embodiment of the present invention, the compound of the formula (I) is the following compound:

{8-fluoro-2-[4-(3-methoxyphenyl)piperazin-1-yl]-3-[2-methoxy-5-(trifluoromethyl)phenyl]-3,4-dihydroquinazolin-4-yl}acetic acid

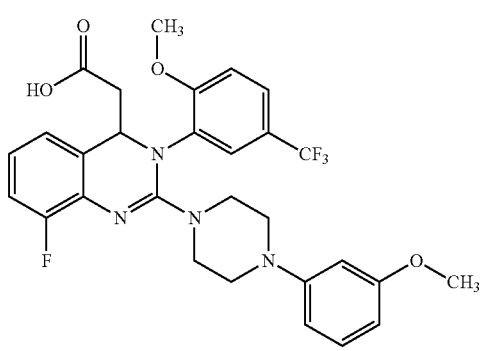 [SMILES: COc1cccc(N2CCN(C3=Nc4c(F)cccc4C(CC(=O)O)N3c3cc(C(F)(F)F)ccc3OC)CC2)c1]

According to a particularly preferred embodiment of the present invention, the compound of the formula (II) is the following compound:

Methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate

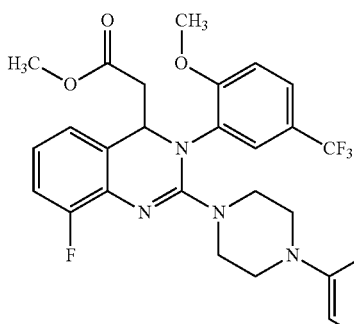

According to a particularly preferred embodiment of the present invention, the compound of the formula (III) is the following compound:

Methyl 2-chloro-8-fluoro-3-[2-methoxy-5-(trifluoromethyl)phenyl]-3,4-dihydroquinazolin-4-yl}-acetate

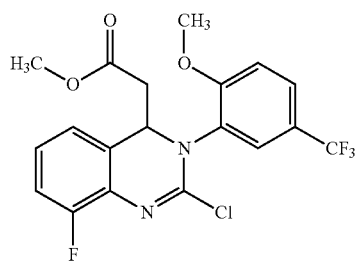

According to a particularly preferred embodiment of the present invention, the compound of the formula (IV) is the following compound:

1-(3-methoxyphenyl)piperazine

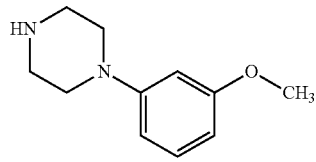

According to a particularly preferred embodiment of the present invention, the compound of the formula (V) is the following compound:

Methyl {8-fluoro-3-[2-methoxy-5-(trifluoromethyl)phenyl]-2-oxo-1,2,3,4-tetrahydroquinazolin-4-yl}acetate

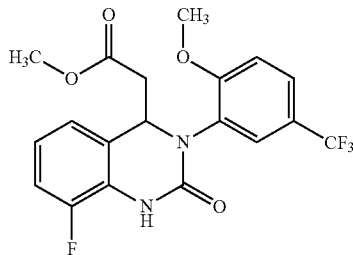 [SMILES: COC(=O)CC1c2cccc(F)c2NC(=O)N1c1cc(C(F)(F)F)ccc1OC]

According to a particularly preferred embodiment of the present invention, the compound of the formula (VI) is the following compound:

N-(2-bromo-6-fluorophenyl)-N'-[2-methoxy-5-(trifluoromethyl)phenyl]urea

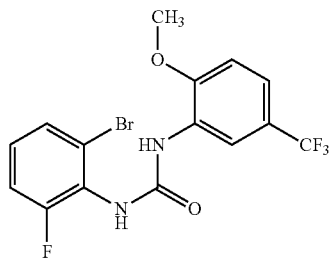 [SMILES: COc1ccc(C(F)(F)F)cc1NC(=O)Nc1c(F)cccc1Br]

According to a particularly preferred embodiment of the present invention, the compound of the formula (VII) is the following compound:

N-(2-fluorophenyl)-N'-[2-methoxy-5-(trifluoromethyl)phenyl]urea

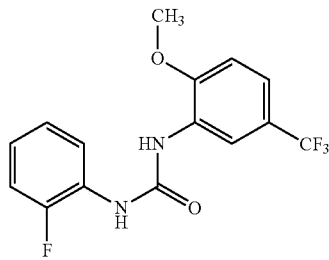 [SMILES: COc1ccc(C(F)(F)F)cc1NC(=O)Nc1ccccc1F]

According to a particularly preferred embodiment of the present invention, the compound of the formula (VIII) is the following compound:

Methyl (2E)-3-{3-fluoro-2-[({[2-methoxy-5-(trifluoromethyl)phenyl]amino}carbonyl)amino]phenyl}acrylate

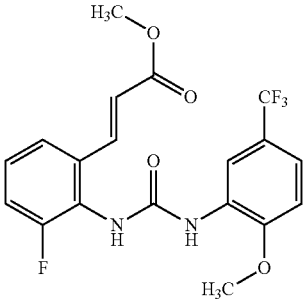 [SMILES: COC(=O)/C=C/c1cccc(F)c1NC(=O)Nc1cc(C(F)(F)F)ccc1OC]

According to a particularly preferred embodiment of the present invention, the compound of the formula (IX) is the following compound:

Methyl Acrylate

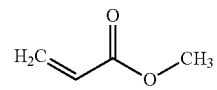

The hydrolysis of the ester of a compound of the formula (II) to a compound of the formula (I) is carried out by reaction of a compound of the formula (II) with a base in an inert solvent, in a temperature range from 18° C. up to reflux of the solvent, preferably at 18 to 50° C., particularly preferably at 20 to 30° C., at normal pressure within, for example, 0.5 to 10 hours, preferably within 1 to 5 hours.

Bases are, for example, alkali metal hydroxides such as sodium hydroxide, lithium hydroxide or potassium hydroxide, or alkali metal carbonates such as caesium carbonate, sodium carbonate or potassium carbonate, or alkoxides such as sodium methoxide or potassium methoxide or sodium ethoxide or potassium ethoxide, the base optionally being present in aqueous solution.

Inert solvents are, for example, ethers such as 1,2-dimethoxyethane, dioxane, tetrahydrofuran, glycol dimethyl ether or diethylene glycol dimethyl ether, alcohols such as methanol, ethanol, n-propanol, isopropanol, n-butanol or tert-butanol, or water, or mixtures of solvents.

Sodium hydroxide in water and dioxane are preferred.

The hydrolysis of the ester of a compound of the formula (II) to a compound of the formula (I) is carried out by reaction of a compound of the formula (II) with an acid in a solvent in the presence of water, in a temperature range from 18° C. up to reflux of the solvent, preferably at 18 to 50° C., particularly preferably at 20 to 30° C., at normal pressure, within, for example, 0.5 to 48 hours, preferably within 5 to 24 hours.

Acids in a solvent are, for example, hydrochloric acid, sulphuric acid or phosphoric acid in dioxane or tetrahydrofuran.

Hydrochloric acid in dioxane is preferred.

The synthesis of a compound of the formula (II) from a compound of the formula (III) and a compound of the formula (IV) in the presence of a base is carried out in an inert solvent, in a temperature range from 40° C. up to reflux of the solvent, preferably under reflux of the solvent, at normal pressure, within, for example, 5 to 48 hours, preferably within 10 to 24 hours.

Bases are, for example, amides such as sodium amide, lithium bis(trimethylsilyl)amide or lithium diisopropylamide, or amine bases such as 1,8-diazabicyclo[5.4.0]undec-7-ene (DBU), 1-(3-methoxyphenyl)piperazine or triethylamine, or other bases such as potassium tert-butoxide or sodium hydride.

Inert solvents are, for example, chlorobenzene or ethers such as 1,2-dimethoxyethane, dioxane, glycol dimethyl ether or diethylene glycol dimethyl ether.

DBU in dioxane is preferred.

The reaction of a compound of the formula (V) to give a compound of the formula (III) is carried out by reaction of a compound of the formula (V) with phosphorus oxychloride, phosphorus trichloride or phosphorus pentachloride, phosphorus oxychloride is preferred, in the presence of a base in an inert solvent, in a temperature range from 40° C. up to reflux of the solvent, preferably under reflux of the solvent, at normal pressure, within, for example, 5 to 48 hours, preferably within 10 to 24 hours.

Bases are, for example, amines such as 1,8-diazabicyclo [5.4.0]undec-7-ene (DBU), pyridine or triethylamine, or amides such as sodium amide, lithium bis(trimethylsilyl)amide or lithium diisopropylamide, or other bases such as potassium tert-butoxide.

Inert solvents are, for example, hydrocarbons such as benzene, xylene, toluene or chlorobenzene.

DBU in chlorobenzene is preferred.

The reaction of a compound of the formula (VI) to give a compound of the formula (V) is carried out by reaction of a compound of the formula (VI) with a compound of the formula (IX) in the presence of a palladium catalyst and of a base in an inert solvent, in a temperature range from 40° C. up to reflux of the solvent, preferably under reflux of the solvent, at normal pressure, within, for example, 5 to 48 hours, preferably within 10 to 24 hours.

Palladium catalysts are, for example, bis(triphenylphosphine)palladium(II) chloride, tetrakis-(triphenylphosphine)palladium(0), bis(tris(o-tolyl)phosphino)palladium(II) chloride or a palladium catalyst prepared from bis(acetonitrile)dichloropalladium or palladium(II) acetate and a ligand, for example, tris(o-tolyl)phosphine, triphenylphosphine or diphenylphosphinoferrocene.

Bases are, for example, 1,8-diazabicyclo[5.4.0]undec-7-ene (DBU), triethylamine or diisopropylethylamine.

Inert solvents are, for example, ethers such as 1,2-dimethoxyethane, dioxane, glycol dimethyl ether or diethylene glycol dimethyl ether, hydrocarbons such as benzene, xylene or toluene, or other solvents such as isobutyronitrile, acetonitrile, nitrobenzene, dimethylformamide, dimethyl-acetamide, dimethyl sulphoxide or N-methylpyrrolidone.

A palladium catalyst prepared from bis(acetonitrile)dichloropalladium and tris(o-tolyl)phosphine and triethylamine in isobutyronitrile is preferred.

The reaction of a compound of the formula (VII) to give a compound of the formula (VIII) is carried out by reaction of a compound of the formula (VII) with a compound of the formula (IX) in acetic acid in the presence of a palladium catalyst, of an oxidizing agent and of an acid, in a temperature range from 0° C. to 50° C., preferably at room temperature, at normal pressure, within, for example, 5 to 48 hours, preferably within 10 to 24 hours.

Palladium catalysts are, for example, palladium salts such as palladium(II) chloride, palladium(II) acetylacetonate, palladium(II) acetate or sodium tetrachloropalladate; palladium (II) acetate is preferred.

Oxidizing agents are, for example, p-benzoquinone or peroxides such as, for example, hydrogen peroxide, tert-butyl hydroperoxide or sodium perborate, or sulphur trioxide pyridine complex, manganese dioxide, 2,3-dichloro-5,6-dicyano-p-benzoquinone (DDQ), sodium peroxodisulphate or oleum (fuming sulphuric acid); p-benzoquinone, sodium peroxodisulphate or oleum (fuming sulphuric acid) are preferred and oleum is particularly preferred.

Acids are, for example, methanesulphonic acid, trifluoromethanesulphonic acid or substituted benzenesulphonic acids, such as, for example, 4-methylbenzenesulphonic acid, 4-chlorobenzene-sulphonic acid or 4-nitrobenzenesulphonic acid, or concentrated sulphuric acid in the form of oleum; trifluoromethanesulphonic acid or sulphuric acid in the form of oleum is preferred, oleum is particularly preferred.

The reaction of a compound of the formula (VIII) to give a compound of the formula (V) is carried out by reaction of a compound of the formula (VIII) with a base in an inert solvent, in a temperature range from 40° C. up to reflux of the solvent, preferably under reflux of the solvent, at normal pressure, within, for example, 1 to 48 hours, preferably within 2 to 14 hours.

Bases are, for example, alkali metal carbonates such as caesium carbonate, sodium carbonate or potassium carbonate, 1,8-diazabicyclo[5.4.0]undec-7-ene (DBU), triethylamine or diisopropylethylamine; potassium carbonate or DBU is preferred.

Inert solvents are, for example, ethers such as 1,2-dimethoxyethane, dioxane, glycol dimethyl ether or diethylene glycol dimethyl ether, or hydrocarbons such as benzene, xylene or toluene, or ketones such as acetone or methyl isobutyl ketone (MIBK), or other solvents such as isobutyronitrile, acetonitrile, chlorobenzene, nitrobenzene, dimethyl formamide, dimethyl-acetamide, dimethyl sulphoxide, N-methylpyrrolidone or tetrahydrothiophene 1,1-dioxide (sulpholane); acetone is preferred.

In addition, the present invention comprises a process for the separation of enantiomers of ($C_1$-$C_4$)-alkyl {8-fluoro-2-[4-(3-methoxyphenyl)piperazin-1-yl]-3-[2-methoxy-5-(trifluoromethyl)phenyl]-3,4-dihydroquinazolin-4-yl}acetate and isolation of ($C_1$-$C_4$)-alkyl (S)-{8-fluoro-2-[4-(3-methoxy-phenyl)piperazin-1-yl]-3-[2-methoxy-5-(trifluoromethyl)phenyl]-3,4-dihydroquinazolin-4-yl}acetate, characterized in that the racemic ester is crystallized with (2S,3S)-2,3-bis[(4-methylbenzoyl)oxy]succinic acid. The crystallization is carried out in a temperature range from 0 to 25° C. in ethyl acetate. The salt of the S enantiomer precipitates from the solution first.

A process for the separation of enantiomers of methyl {8-fluoro-2-[4-(3-methoxyphenyl)piperazin-1-yl]-3-[2-methoxy-5-(trifluoromethyl)phenyl]-3,4-dihydroquinazolin-4-yl}acetate and isolation of methyl (S)-{8-fluoro-2-[4-(3-methoxyphenyl)piperazin-1-yl]-3-[2-methoxy-5-(trifluoromethyl)-phenyl]-3,4-dihydroquinazolin-4-yl}acetate is preferred, characterized in that the racemic ester is crystallized with (2S,3S)-2,3-bis[(4-methylbenzoyl)oxy] succinic acid. The crystallization is carried out in a temperature range from 0 to 25° C. in ethyl acetate. The salt of the S enantiomer precipitates from the solution first.

In addition, the present invention comprises the ($C_1$-$C_4$)-alkyl (S)-{8-fluoro-2-[4-(3-methoxyphenyl)piperazin-1-yl]-3-[2-methoxy-5-(trifluoromethyl)-phenyl]-3,4-dihydroquinazolin-4-yl}acetate(2S,3S)-2,3-bis[(4-methylbenzoyl)oxy]succinic acid salt.

In addition, the present invention comprises the methyl (S)-{8-fluoro-2-[4-(3-methoxyphenyl)piperazin-1-yl]-3-[2-methoxy-5-(trifluoromethyl)-phenyl]-3,4-dihydroquinazolin-4-yl}acetate-(2S,3S)-2,3bis[(4-methylbenzoyl)oxy]succinic acid salt.

In addition, the present invention comprises a process for the racemization of ($C_1$-$C_4$-alkyl (R)-{8-fluoro-2-[4-(3-methoxyphenyl)piperazin-1-yl]-3-[2-methoxy-5-(trifluoromethyl)phenyl]-3,4-dihydroquinazolin-4-yl}acetate, characterized in that in the first stage the alkyl ester is hydrolysed to the acid, in the second stage the acid is racemized using sodium methoxide or sodium ethoxide and in the third stage the acid is again reacted to give the alkyl ester.

A process for the racemization of methyl (R)-{8-fluoro-2-[4-(3-methoxyphenyl)piperazin-1-yl]-3-[2-methoxy-5-(trifluoromethyl)phenyl]-3,4-dihydroquinazolin-4-yl}acetate is preferred, characterized in that in the first stage the methyl ester is hydrolysed to the acid, in the second stage the acid is racemized using sodium methoxide or sodium ethoxide and in the third stage the acid is reacted again to give the methyl ester.

The hydrolysis in the first stage using an acid or a base is carried out under the same reaction conditions as the hydrolysis of the ester of a compound of the formula (II) to give a compound of the formula (I).

The racemization in the second stage is carried out by heating the acid with sodium methoxide or sodium ethoxide, preferably at least 2 equivalents of base being used and sodium methoxide or sodium ethoxide optionally being employed in an alcoholic solution, in a solvent under reflux, at normal pressure, for, for example, 36 to 72 hours, preferably for 50 to 70 hours.

Solvents are, for example, ethers such as 1,2-dimethoxyethane, dioxane, glycol dimethyl ether or diethylene glycol dimethyl ether, hydrocarbons such as benzene, xylene or toluene, or other solvents such as isobutyronitrile, acetonitrile or dimethyl sulphoxide; acetonitrile is preferred.

The esterification in the third stage is carried out, for example, by reaction of the acid with sulphuric acid in methanol or another alcohol under reflux, at normal pressure, for, for example, 12 to 48 hours, preferably for 20 to 30 hours.

In addition, the present invention comprises a process for the racemization of ($C_1$-$C_4$)-alkyl (R)-{8-fluoro-2-[4-(3-methoxyphenyl)piperazin-1-yl]-3-[2-methoxy-5-(trifluoromethyl)phenyl]-3,4-dihydroquinazolin-4-yl}acetate, characterized in that the alkyl ester is reacted with a base in an inert solvent.

A process for the racemization of methyl (R)-{8-fluoro-2-[4-(3-methoxyphenyl)piperazin-1-yl]-3-[2-methoxy-5-(trifluoromethyl)phenyl]-3,4-dihydroquinazolin-4-yl}acetate is preferred, characterized in that the methyl ester is reacted with a base in an inert solvent.

The reaction is carried out in a temperature range from 40° C. up to reflux of the solvent, preferably under reflux of the solvent, at normal pressure, within, for example, 5 to 48 hours, preferably within 12 to 24 hours.

Bases are, for example, organic nitrogen bases such as 1,8-diazabicyclo[5.4.0]undec-7-ene (DBU) or tetramethylguanidine; DBU is preferred.

Inert solvents are, for example, hydrocarbons such as benzene, xylene or toluene, or other solvents such as isobutyronitrile; isobutyronitrile is preferred.

The compounds described in the context of the process according to the invention can also be present in the form of their salts, solvates or solvates of the salts.

The compounds described in the context of the process according to the invention, depending on their structure, can exist in stereoisomeric forms (enantiomers, diastereomers). The process according to the invention therefore also comprises the preparation and the use of the enantiomers or diastereomers and their respective mixtures. The stereoisomerically homogeneous constituents can be isolated from enantiomers and/or diastereomers of this type in a manner known to the person skilled in the art.

The compounds described in the context of the process according to the invention can also, depending on their structure, be present in the form of their tautomers.

Preferred salts in the context of the invention are physiologically acceptable salts of the compounds employed and prepared in the process according to the invention.

Physiologically acceptable salts of the compounds employed and prepared in the process according to the invention comprise acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, malic acid, citric acid, fumaric acid, maleic acid and benzoic acid.

Physiologically acceptable salts of the compounds employed and prepared in the process according to the invention also comprise salts of customary bases, such as, by way of example and preferably, alkali metal salts (e.g. sodium salts and potassium salts), alkaline earth metal salts (e.g. calcium salts and magnesium salts) and ammonium salts, derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietylamine, arginine, lysine, ethylenediamine and methylpiperidine.

Solvates in the context of the invention are designated as those forms of the compounds employed and prepared in the process according to the invention which, in the solid or liquid state, form a complex by coordination with solvent molecules. Hydrates are a special form of the solvates, in which the coordination takes place with water.

In the context of the present invention means racemically that the compounds are not present in enantiomerically pure form, i.e. the compounds are present as mixtures of (S) and (R) enantiomers. The ratio of (S) enantiomer to (R) enantiomer is variable here. A mixture of (S) enantiomer to (R) enantiomer of 1:1 is preferred.

In the context of the present invention, the substituents, if not specified otherwise, have the following meaning:

Alkyl per se and "alk" and "alkyl" in alkoxy, alkylamino, alkylthio, allylcarbonyl, alkylsulphonyl, alkoxycarbonyl and alkylaminosulphonyl represent a linear or branched alkyl radical usually having 1 to 6 ("$C_1$-$C_6$-alkyl"), preferably 1 to 4, particularly preferably 1 to 3 carbon atoms, by way of example and preferably methyl, ethyl, n-propyl, isopropyl, tert-butyl, n-pentyl and n-hexyl.

Alkoxy represents, by way of example and preferably, methoxy, ethoxy, n-propoxy, isopropoxy, tert-butoxy, n-pentoxy and n-hexoxy.

Alkylamino represents an alkylamino radical having one or two (chosen independently of one another) alkyl substituents, by way of example and preferably methylamino, ethylamino, n-propyl-amino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino. $C_1$-$C_3$-Alkylamino represents, for example, a monoalkylamino radical having 1 to 3 carbon atoms or a dialkylamino radical in each case having 1 to 3 carbon atoms per alkyl substituent.

Alkylthio represents, by way of example and preferably, methylthio, ethylthio, n-propylthio, iso-propylthio, tert-butylthio, n-pentylthio and n-hexylthio.

Alkylcarbonyl represents, by way of example and preferably, methylcarbonyl, ethylcarbonyl, n-propylcarbonyl, isopropylcarbonyl, tert-butylcarbonyl, n-pentylcarbonyl and n-hexylcarbonyl.

Alkylsulphonyl represents, by way of example and preferably, methylsulphonyl, ethylsulphonyl, n-propylsulphonyl, isopropylsulphonyl, tert-butylsulphonyl, n-pentylsulphonyl and n-hexylsulphonyl.

Alkoxycarbonyl represents, by way of example and preferably, methoxycarbonyl, ethoxycarbonyl, n-propoxycarbonyl, isopropoxycarbonyl, tert-butoxycarbonyl, n-pentoxycarbonyl and n-hexoxy-carbonyl.

Allcylaminosulphonyl represents an alkylaminosulphonyl radical having one or two (chosen independently of one another) alkyl substituents, by way of example and preferably methylaminosulphonyl, ethylaminosulphonyl, n-propylaminosulphonyl, isopropylaminosulphonyl, tert-butylaminosulphonyl, n-pentylaminosulphonyl, n-hexylaminosulphonyl, N,N-dimethyl-aminosulphonyl, N,N-diethylaminosulphonyl, N-ethyl-N-methylaminosulphonyl, N-methyl-N-n-propylaminosulphonyl, N-isopropyl-N-n-propylaminosulphonyl, N-tert-butyl-N-methylamino-sulphonyl, N-ethyl-N-n-pentylaminosulphonyl and N-n-hexyl-N-methylaminosulphonyl. $C_1$-$C_3$-Alkylaminosulphonyl represents, for example, a monoalkylaminosulphonyl radical having 1 to 3 carbon atoms or a diallylaminosulphonyl radical in each case having 1 to 3 carbon atoms per alkyl substituent.

Aryl represents a mono- or bicyclic aromatic, carbocyclic radical usually having 6 to 10 carbon atoms; by way of example and preferably phenyl and naphthyl.

Halogen represents fluorine, chlorine, bromine and iodine.

The present invention is described below by means of non-restrictive preferred examples and comparison examples. If not stated otherwise, all quantitative data relate to percentages by weight.

WORKING EXAMPLES

Abbreviation Index
ACN acetonitrile
API-ES-pos. atmospheric pressure ionization, electrospray, positive (in MS)
API-ES-neg. atmospheric pressure ionization, electrospray, negative (in MS)
ca. about
CI, $NH_3$ chemical ionization (with ammonia)
DBU 1,8-diazabicyclo[5.4.0]undec-7-ene
DMAP 4-(dimethylamino)pyridine
DMSO dimethyl sulphoxide
ESTD external standardization
h hour(s)
HPLC high pressure liquid chromatography
conc. concentrated
MIBK methyl isobutyl ketone
min. minutes
MS mass spectroscopy
NMR nuclear magnetic resonance spectroscopy
$R_T$ retention time (in HPLC)
VDO vacuum drying oven
General Methods HPLC:

Method 1 (HPLC): Instrument: HP 1050 with multiple wavelength detection; column: Phenomenex-Prodigy ODS (3) 100 A, 150 mm×3 mm, 3 µm; eluent A: (1.0 g of $KH_2PO_4$+ 1.0 ml of $H_3PO_4$)/l water, eluent B: acetonitrile; gradient: 0 min 10% B, 25 min 80% B, 35 min 80% B; flow: 0.5 ml/min; temp.: 45° C.; UV detection: 210 nm.

Method 2 (HPLC): Instrument: HP 1050 with variable wavelength detection; column: Chiral AD-H, 250 mm×4.6 mm, 5 µm; eluent A: n-heptane +0.2% diethylamine, eluent B: isopropanol +0.2% diethylamine; gradient: 0 min 12.5% B, 30 min 12.5% B; flow: 1 ml/min; temp.: 25° C.; UV detection: 250 nm.

For the S enantiomer, positive e.e. values are indicated, for the R enantiomer negative values.

Method 3 (HPLC): Instrument: HP 1050 with variable wavelength detection; column: chiral AD-H, 250 mm×4.6 mm, 5 µm; eluent A: n-heptane +0.2% diethylamine, eluent B: isopropanol+0.2% diethylamine; gradient: 0 min 25% B, 15 min 25% B; flow: 1 ml/min; temp.: 30° C.; UV detection: 250 nm.

For the S enantiomer, positive e.e. values are indicated, for the R enantiomer negative values.

Method 4 (HPLC): Instrument: HP 1100 with variable wavelength detection; column: Phenomenex-Prodigy C8, 150 mm×3 mm, 5 µm; eluent A: (1.36 g of $KH_2PO_4$+1.15 g of 85% strength $H_3PO_4$)/l of water, eluent B: acetonitrile; gradient: 0 min 10% B, 20 min 80% B, 30 min 80% B; flow: 0.5 ml/min; temp.: 40° C.; UV detection: 210 nm.

Yields indicated are not corrected in terms of content.

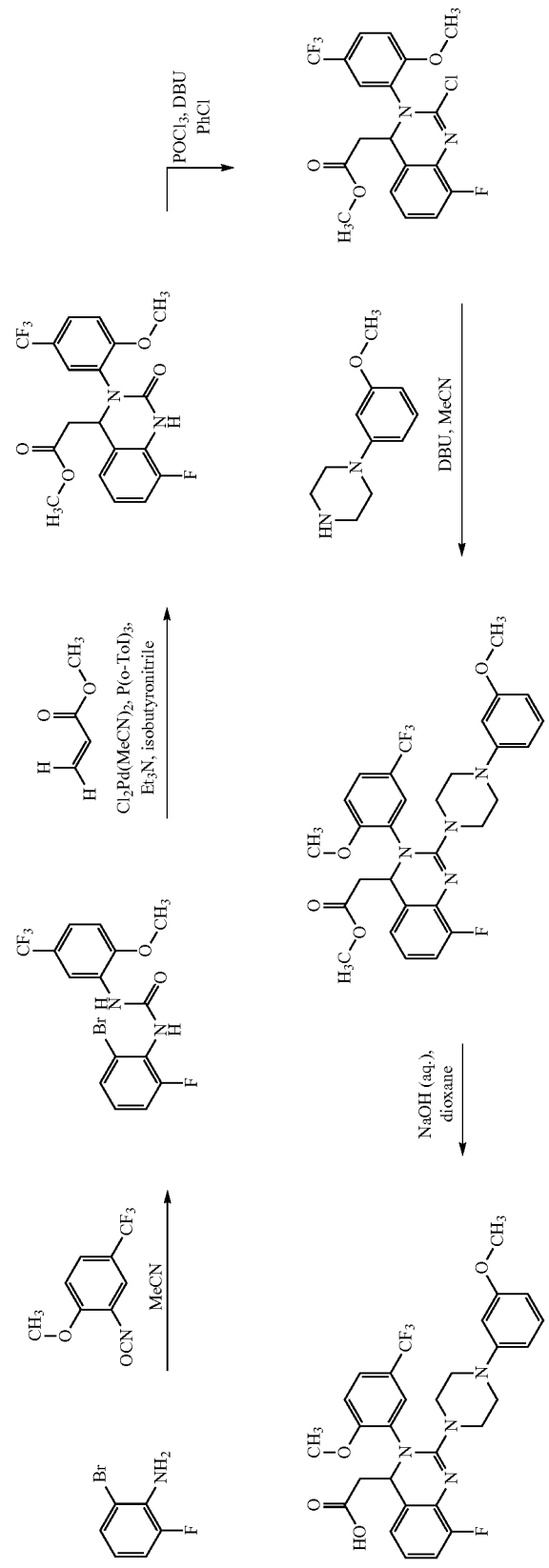
Scheme 5: Synthesis of {8-fluoro-2-[4-(3-methoxyphenyl)piperazin-1-yl]-3-[2-methoxy-5-(trifluoromethyl)-phenyl]-3,4-dihydroquinazolin-4-yl}acetic acid

Example 1

N-(2-Bromo-6-fluorophenyl)-N'-[2-methoxy-5-(trifluoromethyl)phenyl]urea

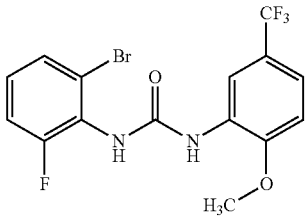 [SMILES: COc1ccc(C(F)(F)F)cc1NC(=O)Nc1c(F)cccc1Br]

2-Methoxy-5-trifluoromethylphenyl isocyanate (274.3 g) is dissolved in acetonitrile (1 l), then 2-bromo-6-fluoroaniline (200 g) is added and rinsed out with acetonitrile (50 ml). The resulting clear solution is stirred under reflux (ca. 85° C.) for 38 h, then concentrated in vacuo at 40° C. to a viscous magma. This is filtered off with suction, washed with acetonitrile (260 ml, cooled to 0-5° C.) and dried overnight at 45° C. in the VDO using entraining nitrogen. A total of 424.3 g of N-(2-bromo-6-fluorophenyl)-N'-[2-methoxy-5-(trifluoromethyl)phenyl]urea are obtained as a solid, corresponding to 99.2% of theory.

$^1$H NMR (300 MHz, $d_6$-DMSO): δ=8.93 (s, 1H), 8.84 (s, 1H), 8.52 (d, $^3$J=2.3, 2H), 7.55 (d, $^2$J=7.7, 1H), 7.38-7.26 (m, 3H), 7.22 (d, $^2$J=8.5, 1H), 4.00 (s, 3H) ppm;

MS (API-ES-pos.): m/z=409 [(M+H)$^+$, 100%];

HPLC (method 1): $R_T$=22.4 and 30.6 min.

Example 2

N-(2-Bromo-6-fluorophenyl)-N'-[2-methoxy-5-(trifluoromethyl)phenyl]urea (Alternative Synthesis)

2-Methoxy-5-trifluoromethylphenyl isocyanate (1.19 kg) is fused at about 35° C. and dissolved in acetonitrile (4.2 l), then 2-bromo-6-fluoroaniline (870 g) is added and rinsed out with acetonitrile (380 ml). The resulting clear solution is stirred at 74-88° C. for 45 h, then concentrated in vacuo (200 mbar) at 50° C. to give a viscous magma (amount of distillate 4.4 l). This is diluted at room temperature with diisopropyl ether (1.5 l), filtered off with suction, washed with diisopropyl ether (1.15 l) and dried at 45° C. in the VDO using entraining nitrogen to constant mass (24 h). A total of 1.63 kg of N-(2-bromo-6-fluorophenyl)-N'-[2-methoxy-5-(trifluoromethyl)phenyl]urea is obtained as a solid, corresponding to 87.5% of theory.

HPLC (method 1): $R_T$=22.6 and 30.8 min.

Example 3

Methyl {8-fluoro-3-[2-methoxy-5-(trifluoromethyl)phenyl]-2-oxo-1,2,3,4-tetrahydroquinazolin-4-yl}acetate

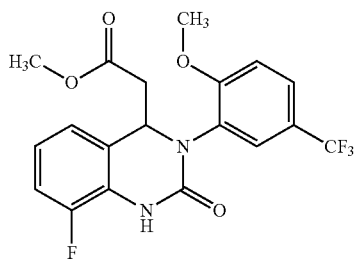 [SMILES: COC(=O)CC1c2cccc(F)c2NC(=O)N1c1cc(C(F)(F)F)ccc1OC]

N-(2-Bromo-6-fluorophenyl)-N'-[2-methoxy-5-(trifluoromethyl)phenyl]urea (300 g) is suspended in isobutyronitrile (1.2 l) under a nitrogen atmosphere, then triethylamine (210 ml), bis(acetonitrile)dichloropalladium (7.5 g), tris-(o-tolyl)phosphine (18.0 g) and methyl acrylate (210 ml) are added in this sequence. The resulting suspension is stirred under reflux (ca. 102° C.) for 16 h and then cooled to room temperature. Water (1.2 l) is added and the mixture is stirred at room temperature for 1 h, then filtered off with suction and washed with water/methanol (1:1, 300 ml) and acetonitrile (100 ml). The residue is dried overnight at 45° C. in the VDO using entraining nitrogen. A total of 208 g of methyl {8-fluoro-3-[2-methoxy-5-(trifluoromethyl)phenyl]-2-oxo-1,2,3,4-tetrahydroquinazolin-4-yl}acetate are obtained as a solid, corresponding to 68.5% of theory.

$^1$H NMR (300 MHz, $d_6$-DMSO): δ=9.73 (s, 1H), 7.72 (d, $^2$J=7.3, 1H), 7.71 (s, 1H), 7.33 (d, $^2$J=9.3, 1H), 7.15 (dd, $^2$J=9.6, $^2$J=8.6, 1H), 7.01 (d, $^2$J=−7.3, 1H), 6.99-6.94 (m, 1H), 5.16 (t, $^2$J=5.9, 1H), 3.84 (s, 3H), 3.41 (s, 3H), 2.81 (dd, $^2$J=15.4, $^2$J=5.8, 1H), 2.62 (dd, $^2$J=15.4, $^2$J=6.3, 1H) ppm;

MS (API-ES-pos.): m/z=413 [(M+H)$^+$, 100%], 825 [(2M+H)$^+$, 14%];

HPLC (method 1): $R_T$=19.3 min; Pd (ICP): 16 000 ppm.

Example 4

Methyl {8-fluoro-3-[2-methoxy-5-(trifluoromethyl)phenyl]-2-oxo-1,2,3,4-tetrahydroquinazolin-4-yl}acetate (Alternative Synthesis)

N-(2-Bromo-6-fluorophenyl)-N'-[2-methoxy-5-(trifluoromethyl)phenyl]urea (2.5 kg) is suspended in isobutyronitrile under a nitrogen atmosphere (9 l), then triethylamine (1.31 kg), bis(acetonitrile)dichloropalladium (64.9 g), tris(o-tolyl)phosphine (149 g) and methyl acrylate (1.59 kg) are added in this sequence. The resulting suspension is stirred at 90-100° C. for 22 h, then cooled to room temperature. Water (9 l) is added and the mixture is stirred at room temperature for 1 h, then the solid is filtered off with suction and washed with water/methanol (1:1, 2.5 l) and acetonitrile (850 ml). The residue is dried overnight at 45° C. in the VDO to constant mass (21 h) using entraining nitrogen. A total of 1.90 kg of methyl {8-fluoro-3-[2-methoxy-5-(trifluoromethyl)phenyl]-2-oxo-1,2,3,4-tetrahydroquinazolin-4-yl}acetate are obtained as a solid, corresponding to 74.9% of theory.

HPLC (method 1): $R_T$=19.4 min.

Example 5

Methyl {2-chloro-8-fluoro-3-[2-methoxy-5-(trifluoromethyl)phenyl]-3,4-dihydroquinazolin-4-yl}acetate/chlorination

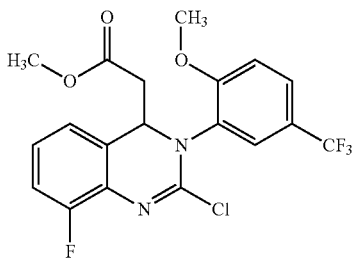 [SMILES: COC(=O)CC1c2cccc(F)c2N=C(Cl)N1c1cc(C(F)(F)F)ccc1OC]

A solution of 2.84 kg of methyl {8-fluoro-3-[2-methoxy-5-(trifluoromethyl)phenyl]-2-oxo-1,2,3,4-tetrahydroquinazolin-4-yl}acetate in 14.8 l of chlorobenzene is heated to reflux and the solvent is distilled off until water no longer separates. The mixture is cooled to 120° C. 3.17 kg of phosphorus oxychloride are added in the course of 10 min, and subsequently 2.10 kg of DBU are added within a further 10 min. The mixture is heated at reflux for 9 hours.

For work-up, it is cooled to 40° C., stirred overnight and the vessel contents are added to 11.4 l of water which has previously been adjusted to 40° C. During the addition, an internal temperature of 40-45° C. should be maintained. The mixture is allowed to cool to room temperature, 11.4 l of dichloromethane are added, the mixture is filtered through a Seitz filter plate and the phases are separated. The organic phase is washed with 11.4 l of water, 11.4 l of an aqueous saturated sodium hydrogencarbonate solution and again with 11.4 l of water. The organic phase is concentrated in vacuo in a rotary evaporator and the residue which remains (2.90 kg) is employed in the next stage without further treatment.

$^1$H NMR (300 MHz, d$_6$-DMSO): δ=7.93-7.82 (m, 2H), 7.38 (d, $^2$J=8.9, 1H), 7.17 (m, 2H), 6.97-6.91 (m, 1H), 5.45 and 5.29 (m and t, $^2$J=5.4, 1H), 3.91 and 3.84 (2s, 3H), 3.48 (s, 3H), 3.0-2.6 (m, 2H) ppm;

MS (CI, NH$_3$): m/z=431 [(M+H)$^+$, 100%];

HPLC (method 1): R$_T$=23.5 min; typical Pd value (ICP): 170 ppm.

Example 6

Methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate/amination

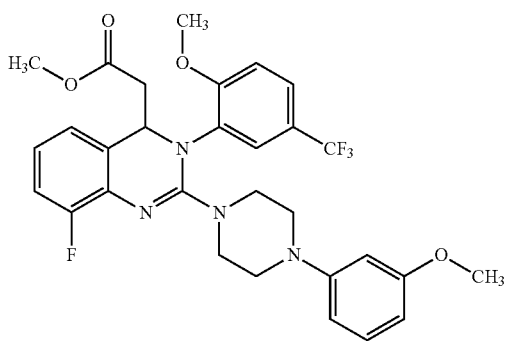 [SMILES: COC(=O)CC1c2cccc(F)c2N=C(N2CCN(c3cccc(OC)c3)CC2)N1c1cc(C(F)(F)F)ccc1OC]

Methyl {2-chloro-8-fluoro-3-[2-methoxy-5-(trifluoromethyl)phenyl]-3,4-dihydroquinazolin-4-yl}acetate (52.5 g) is dissolved in 1,4-dioxane (100 ml), 3-methoxyphenylpiperazine (25.8 g) and DBU (20.4 g) are added at room temperature, the temperature increasing. The mixture is stirred under reflux for 22 h, then cooled to room temperature, diluted with ethyl acetate (500 ml) and water (200 ml) and the phases are separated. The organic phase is washed with 0.2N hydrochloric acid (three times 100 ml) and water (200 ml), dried over sodium sulphate and concentrated in a rotary evaporator. A total of 62.5 g of methyl {8-fluoro-2-[4-(3-methoxyphenyl)piperazin-1-yl]-3-[2-methoxy-5-(trifluoromethyl)phenyl]-3,4-dihydroquinazolin-4-yl}acetate is obtained as a solidified foam, which is reacted as the crude product without further purification.

HPLC (method 1): R$_T$=16.6 min.

Example 7

Methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate/one-pot Chlorination+Amination Methyl {8-fluoro-3-[2-methoxy-5-(trifluoromethyl)phenyl]-2-oxo-1,2,3,4-tetrahydroquinazolin-4-yl}acetate (50.0 g) is initially introduced in chlorobenzene (300 ml), then chlorobenzene is partially distilled off (50 ml). The mixture is cooled to 120° C., DBU (36.9 g) is added, then phosphorus oxychloride (33.4 ml) is metered in at 120-128° C. over the course of 10 min. The mixture is stirred under reflux (ca. 130° C.) for 9 h. Subsequently, it is cooled to 40° C., slowly treated with water (200 ml) at 40-45° C., cooled to room temperature and diluted with dichloromethane (200 ml), extracted with stirring and the phases are then separated. The organic phase is washed with water (200 ml), saturated aqueous sodium hydrogencarbonate solution (200 ml) and water (200 ml) again, dried over sodium sulphate, concentrated in a rotary evaporator and then dried at 50° C. in a high vacuum. The residue (48.1 g) is dissolved in chlorobenzene (20 ml), then the solution is diluted with 1,4-dioxane (80 ml) and 3-methoxyphenylpiperazine (23.6 g) and DBU (18.7 g) are added at room temperature, the temperature increasing. The mixture is stirred under reflux for 22 h, then cooled to room temperature, diluted with ethyl acetate (500 ml) and water (200 ml) and the phases are separated. The organic phase is washed with 0.2N hydrochloric acid (three times 100 ml) and water (200 ml), dried over sodium sulphate and concentrated in a rotary evaporator. A total of 55.6 g of methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate are obtained as a solidified foam, which is reacted without further purification as the crude product.

HPLC (method 1): R$_T$=16.2 min.

Example 8

(±)-{8-Fluoro-2-[4-(3-methoxyphenyl)piperazin-1-yl]-3-(2-methoxy-5-trifluoromethylphenyl)-3,4-dihydroquinazolin-4-yl}acetic acid/hydrolysis of Racemate

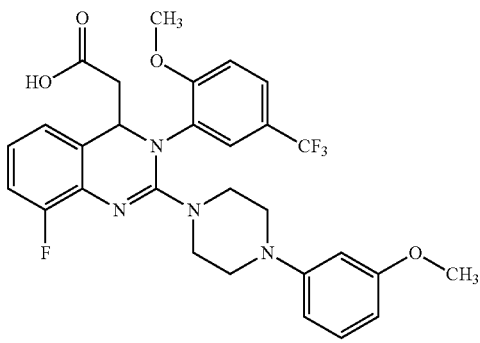 [SMILES: COc1cccc(N2CCN(C3=Nc4c(F)cccc4C(CC(=O)O)N3c3cc(C(F)(F)F)ccc3OC)CC2)c1]

Methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate (64 g) is dissolved in 1,4-dioxane (450 ml) and 1N sodium hydroxide solution (325 ml) and stirred at room temperature for 2 h, then some of the solvent is distilled off at 30° C. in vacuo (400 ml). Subsequently, toluene (300 ml) is added and the phases are separated. The aqueous phase is washed with toluene (twice 150 ml), then the combined organic phases are extracted again with 1N sodium hydroxide solution (50 ml). The pH of the combined aqueous phases is adjusted to 7.5 with 2N hydrochloric acid (ca. 150 ml), then MIBK (150 ml) is added. The phases are separated, the aqueous phases are extracted again with MIBK (150 ml), then the combined MIBK phases are dried over sodium sulphate and concentrated at 45° C. A total of 64 g of (±)-{8-fluoro-2-[4-(3-methoxyphenyl)piperazin-1-yl]-3-(2-methoxy-5-trifluoromethylphenyl)-3,4-dihydroquinazolin-4-yl}acetic acid are obtained in quantitative yield as an amorphous solid.

HPLC (method 1): $R_T$=14.9 min.

Scheme 6: Separation of enantiomers of methyl {8-fluoro-2-[4-(3-methoxyphenyl)piperazin-1-yl]-3-[2-methoxy-5-(trifluoromethyl)phenyl]-3,4-dihydroquinazolin-4-yl}acetate

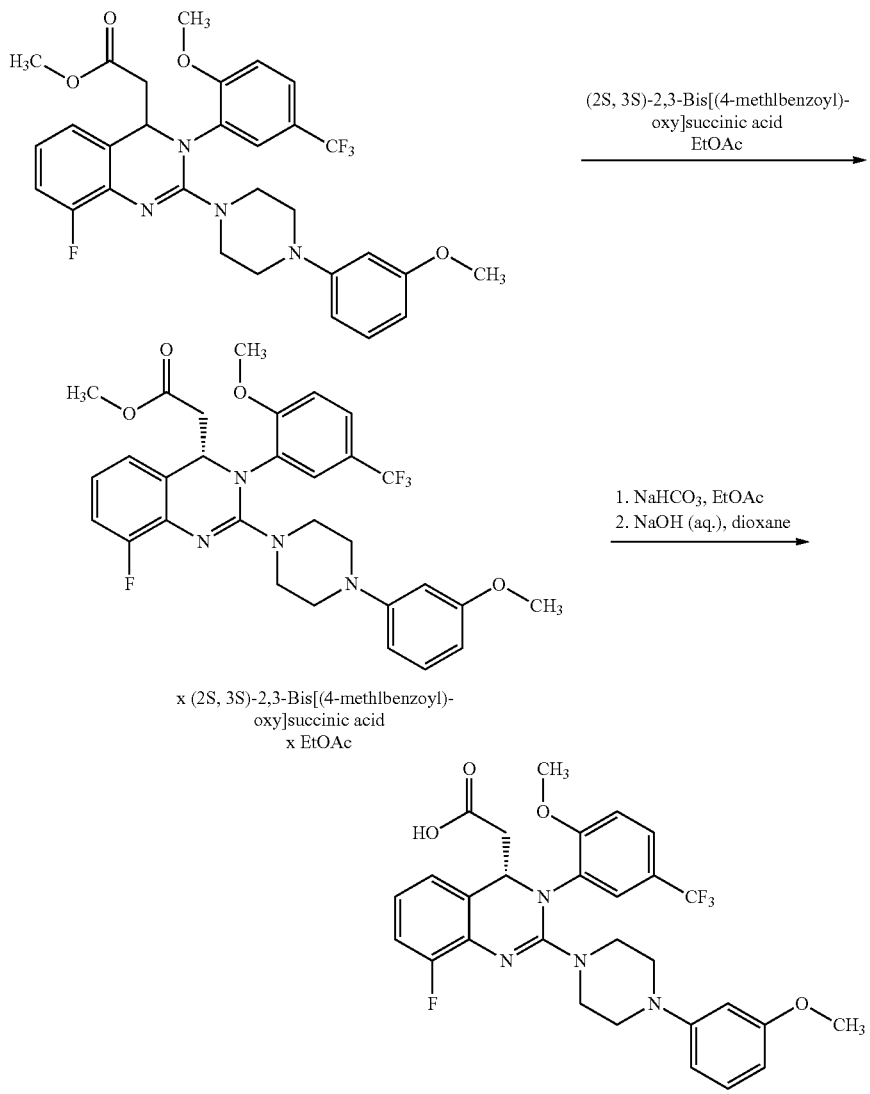

Example 9

(2S,3S)-2,3-Bis[(4-methylbenzoyl)oxy]succinic acid-methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate (1:1-salt)/crystallization

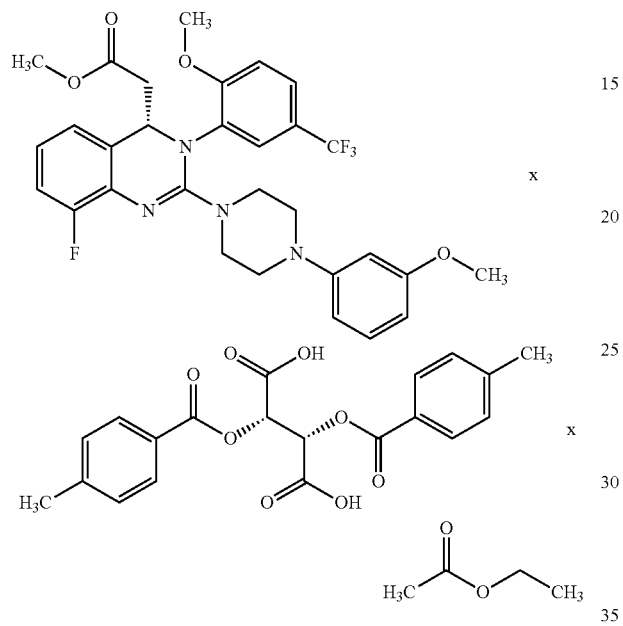

Methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate (62.5 g, crude product) is dissolved in ethyl acetate (495 ml) and filtered. (2S,3S)-2,3-Bis[(4-methylbenzoyl)oxy]succinic acid (42.0 g) is added to the filtrate, the mixture is stirred at room temperature for 30 min, then it is seeded with (2S,3S)-2,3-bis[(4-methylbenzoyl)oxy]-succinic acid-methyl {8-fluoro-2-[4-(3-methoxyphenyl)piperazin-1-yl]-3-[2-methoxy-5-(trifluoromethyl)phenyl]-3,4-dihydroquinazolin-4-yl}acetate (1:1 salt) (165 mg) and stirred at room temperature for 3 days, subsequently cooled to 0-3° C. and stirred for a further 3 h. The suspension is filtered off with suction and washed with cold ethyl acetate (0-10° C., 35 ml). The crystals are dried at 40° C. for 18 h in the VDO using entraining nitrogen. A total of 37.1 g of the salt are thus obtained as a solid, corresponding to 30.4% of theory over three stages (chlorination, amination and crystallization) based on the racemate, or 60.8% based on the resulting S enantiomer.

$^1$H NMR (300 MHz, $d_6$-DMSO): δ=7.90 (d, $^2$J=7.8, 4H), 7.56 (d, $^2$J=8.3, 1H), 7.40 (d, $^2$J=7.8, 4H), 7.28-7.05 (m, 4H), 6.91-6.86 (m, 2H), 6.45 (d, $^2$J=8.3, 1H), 6.39-6.36 (m, 2H), 5.82 (s, 2H), 4.94 (m, 1H), 4.03 (q, $^2$J=7.1, 2H), 3.83 (brs, 3H), 3.69 (s, 3H), 3.64 (s, 3H), 3.47-3.36 (m, 8H and water, 2H), 2.98-2.81 (m, 5H), 2.58-2.52 (m, 1H), 2.41 (s, 6H), 1.99 (s, 3H), 1.18 (t, $^2$J=7.2, 3H) ppm;

HPLC (method 1): $R_T$=16.6 and 18.5 min.

Example 10

(2S,3S)-2,3-Bis[(4-methylbenzoyl)oxy]succinic acid-methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate (1:1 salt)/recrystallization (2S,3S)-2,3-Bis[(4-methylbenzoyl)oxy]succinic acid-methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate (1:1 salt) (36.8 g) is suspended in ethyl acetate (370 ml) and dissolved by heating to reflux (77° C.). The mixture is slowly cooled to room temperature. Spontaneous crystallization takes place in the course of this. The suspension is stirred at RT for 16 h, subsequently cooled to 0-5° C. and stirred for a further 3 h. The suspension is filtered off with suction and washed twice with cold ethyl acetate (0-10° C., two times 15 ml). The crystals are dried at 45° C. for 18 h in the VDO using entraining nitrogen. A total of 33.6 g of the salt are thus obtained as a solid, corresponding to 91.3% of theory.

HPLC (method 1): $R_T$=16.9 and 18.8 min.;
HPLC (method 3): 99.9% e.e.

Example 11

(S)-{8-Fluoro-2-[4-(3-methoxyphenyl)piperazin-1-yl]-3-(2-methoxy-5-trifluoromethylphenyl)-3,4-dihydroquinazolin-4-yl}acetic acid

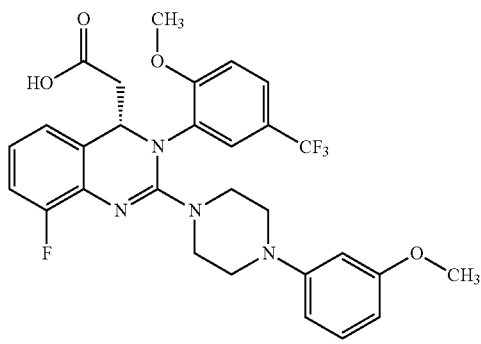

(2S,3S)-2,3-Bis[(4-methylbenzoyl)oxy]succinic acid-methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate (1:1 salt) (10.1 g, containing 14 ppm of Pd) are suspended in ethyl acetate (100 ml) and shaken with saturated aqueous sodium bicarbonate solution (100 ml) until both phases are clear. The phases are separated and the organic phase is concentrated in a rotary evaporator. The residue is dissolved in 1,4-dioxane (100 ml) and 1N sodium hydroxide solution (31.2 ml) and stirred at room temperature for 3 h. Subsequently, the pH is adjusted to 7.5 using 1N hydrochloric acid (ca. 17 ml), MIBK (80 ml) is added, then the pH is readjusted to 7.0 using 1N hydrochloric acid (ca. 2 ml). The phases are separated, and the organic phase is dried over sodium sulphate and concentrated. The residue is dissolved in ethanol (40 ml) and concentrated, then dissolved in ethanol (40 ml) again and concentrated and dried at 50° C. in a high vacuum. The solidified foam is dried at 45° C. for 18 h in the VDO using entraining nitrogen. A total of 5.05 g of (S)-{8-fluoro-2-[4-(3-methoxyphenyl)piperazin-1-yl]-3-(2- methoxy-5-trifluoromethylphenyl)-3,4-dihydroquinazolin-4-yl}acetic acid are obtained as an amorphous solid, corresponding to 85.0% of theory.

$^1$H NMR (300 MHz, d$_6$-DMSO): δ=7.53 (d, $^2$J=8.4, 1H), 7.41 (brs, 1H), 7.22 (d, $^2$J=8.5, 1H), 7.09-7.01 (m, 2H), 6.86 (m, 2H), 6.45 (dd, $^2$J=8.2, $^3$J=1.8, 1H), 6.39-6.34 (m, 2H), 4.87 (t, $^2$J=7.3, 1H), 3.79 (brs, 3H), 3.68 (s, 3H), 3.50-3.38 (m, 4H), 2.96-2.75 (m, 5H), 2.45-2.40 (m, 1H) ppm;

MS (API-ES-neg.): m/z=571 [(M−H), 100%];
HPLC (method 1): R$_T$=15.1 min;
HPLC (method 2): 99.8% e.e.; Pd (ICP): <1 ppm.

Example 12

(2R,3R)-2,3-Bis[(4-methylbenzoyl)oxy]succinic acid-methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate (1:1 salt)/ crystallization of R Isomer from Mother Liquor

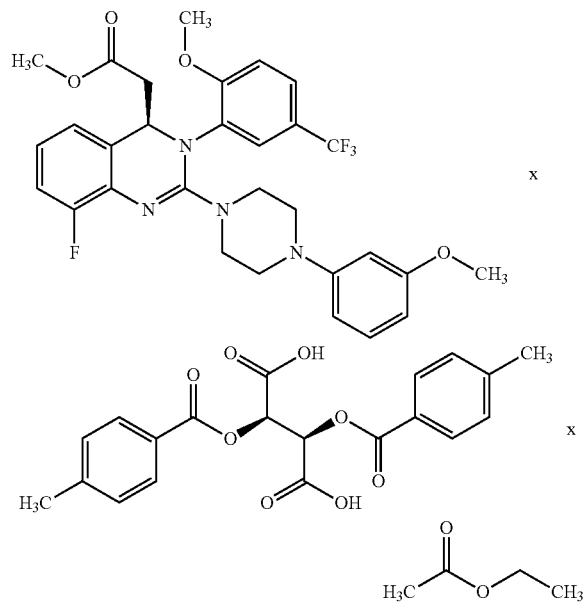

The mother liquor from a crystallization of (2S,3S)-2,3-bis [(4-methylbenzoyl)oxy]succinic acid-methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate (1:1 salt) on a 279 g scale is shaken with saturated aqueous sodium bicarbonate solution (1.5 l), the phases are separated and the organic phase is shaken with semi-saturated aqueous sodium bicarbonate solution (1.5 l). The phases are separated, and the organic phase is dried over sodium sulphate and concentrated in a rotary evaporator. The residue (188.4 g) is dissolved in ethyl acetate (1.57 l), then (2R,3R)-2,3-bis[(4-methylbenzoyl)oxy]succinic acid (121.7 g) is added and the mixture is stirred at room temperature for 10 min. Subsequently, it is seeded with (2R,3R)-2,3-bis[(4-methylbenzoyl) oxy]succinic acid-methyl {8-fluoro-2-[4-(3-methoxyphenyl) piperazin-1-yl]-3-[2-methoxy-5-(trifluoromethyl)phenyl]-3,4-dihydroquinazolin-4-yl}acetate (1:1 salt) (0.38 g) and stirred at room temperature for 18 h, subsequently cooled to 0-3° C. and stirred for a further 3 h. The suspension is filtered off with suction and washed with cold ethyl acetate (0-10° C., 500 ml). The crystals are dried at 40° C. for 18 h in the VDO using entraining nitrogen. A total of 160 g of the salt are thus obtained as a solid.

HPLC (method 1): R$_T$=16.6 and 18.5 min.;
HPLC (method 3): −99.0% e.e.

Example 13

(R)-{8-Fluoro-2-[4-(3-methoxyphenyl)piperazin-1-yl]-3-(2-methoxy-5-trifluoromethylphenyl)-3,4-dihydroquinazolin-4-yl}acetic acid/preparation of R Isomer

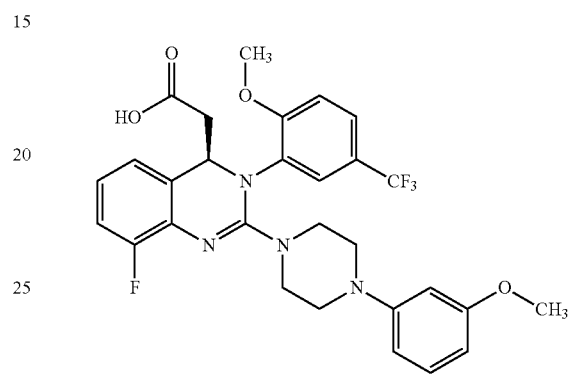

(2R,3R)-2,3-Bis [(4-methylbenzoyl)oxy]succinic acid-methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate (1:1 salt) (170 g) are suspended in ethyl acetate (850 ml) and shaken with saturated aqueous sodium bicarbonate solution (850 ml) until both phases are clear (ca. 5 min.). The phases are separated, and the solvent of the organic phase is replaced at normal pressure with 1,4-dioxane up to a final temperature of 99° C. (a total of 2.55 l of solvent is distilled off and 2.55 l of 1,4-dioxane are employed in portions). The mixture is cooled to room temperature and stirred at room temperature for 18 h with 1N sodium hydroxide solution (525 ml). Subsequently, the pH is adjusted to 7.5 using concentrated hydrochloric acid (ca. 35 ml), MIBK (850 ml) is added, then the pH is readjusted to 7.0 using concentrated hydrochloric acid (ca. 10 ml). The phases are separated, and the organic phase is dried over sodium sulphate and concentrated. The residue is dissolved in ethanol (350 ml) and concentrated, then again dissolved in ethanol (350 ml) and concentrated at 50° C. A total of 91.6 g of (R)-{8-fluoro-2-[4-(3-methoxyphenyl)piperazin-1-yl]-3-(2-methoxy-5-trifluoromethylphenyl)-3,4-dihydroquinazolin-4-yl}acetic acid are thus obtained as an amorphous solid, corresponding to 91.6% of theory.

HPLC (method 1): R$_T$=14.8 min.

Example 14

{8-Fluoro-2-[4-(3-methoxyphenyl)piperazin-1-yl]-3-(2-methoxy-5-trifluoromethylphenyl)-3,4-dihydroquinazolin-4-yl}acetic acid/racemization of R Enantiomer (R)-{8-Fluoro-2-[4-(3-methoxyphenyl)piperazin-1-yl]-3-(2-methoxy-5-trifluoromethyl-phenyl)-3,4-dihydroquinazolin-4-yl}acetic acid (50 g) is dissolved in acetonitrile (500 ml) and treated with sodium methoxide (30% strength in methanol, 32.4 ml) and then stirred under reflux for 60 h. After cooling to room temperature, the mixture is concentrated to one half in vacuo, then it is adjusted to pH 7.5 using hydrochloric acid (20% strength, ca. 20 ml), MIBK (200 ml) is added and it is readjusted to pH 7 using hydrochloric acid (20% strength). The phases are separated, and the organic phase is dried over sodium sulphate and concentrated in a rotary evaporator to give a hard foam. The residue is dissolved in ethanol (150 ml) and concentrated, then again dissolved in ethanol (150 ml) and concentrated. A total of 54.2 g of (±)-{8-fluoro-2-[4-(3-methoxyphenyl)piperazin-1-yl]-3-(2-methoxy-5-trifluoromethylphenyl)-3,4-dihydroquinazolin-4-yl}acetic acid are thus obtained in quantitative yield as an amorphous solid.

HPLC (method 1): $R_T$=14.9 min.;
HPLC (method 4): 80.8% by weight.

Example 15

Methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate/esterification of Racemate (±)-{8-Fluoro-2-[4-(3-methoxyphenyl)piperazin-1-yl]-3-(2-methoxy-5-trifluoromethylphenyl)-3,4-dihydroquinazolin-4-yl}acetic acid (54 g) is dissolved in methanol (540 g), then concentrated sulphuric acid (7.85 ml) is added. The mixture is stirred under reflux for 26 h, then cooled and concentrated in vacuo to ca. one third of the original volume. Water (150 ml) and dichloromethane (150 ml) are added, then the phases are separated. The organic phase is extracted with saturated sodium hydrogencarbonate solution (two times 140 ml), dried over sodium sulphate and concentrated to give a foamy residue. This is dissolved twice in succession in ethanol (150 ml each) and concentrated, and subsequently dried for 18 h in vacuo using entraining nitrogen. A total of 41.6 g of methyl {8-fluoro-2-[4-(3-methoxyphenyl)piperazin-1-yl]-3-[2-methoxy-5-(trifluoromethyl)phenyl]-3,4-dihydroquinazolin-4-yl}acetate are thus obtained as an amorphous solid, corresponding to 75.2% of theory.

HPLC (method 1): $R_T$=16.8 min.;
HPLC (method 4): 85.3% by weight;
HPLC (method 3): −8.5% e.e.

Example 16

(2S,3S)-2,3-Bis[(4-methylbenzoyl)oxy]succinic acid-methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate (1:1 salt)/crystallization of esterified racemate Methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate (41.0 g) is suspended in ethyl acetate (287 ml), then (2S,3S)-2,3-bis[(4-methylbenzoyl)oxy]succinic acid (27.5 g) is added. The mixture is stirred at room temperature for 30 min, then it is seeded with (2S,3S)-2,3-bis[(4-methylbenzoyl)oxy]succinic acid-methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate (1:1 salt) (0.08 g). The suspension is stirred at RT for 16 h, subsequently cooled to 0-5° C. and stirred for a further 3 h, then filtered off with suction and washed with cold ethyl acetate (0-10° C., four times 16 ml). The crystals are dried at 45° C. for 18 h in the VDO using entraining nitrogen. A total of 25.4 g of the salt are thus obtained as a solid, corresponding to 37.4% of theory.

HPLC (method 1): $R_T$=16.9 and 18.8 min.;
HPLC (method 4): 99.5% by weight;
HPLC (method 3): 99.3% e.e.

Example 17

(S)-{8-Fluoro-2-[4-(3-methoxyphenyl)piperazin-1-yl]-3-(2-methoxy-5-trifluoromethylphenyl)-3,4-dihydroquinazolin-4-yl}acetic acid/hydrolysis of Crystallizate (2S,3S)-2,3-Bis[(4-methylbenzoyl)oxy]succinic acid-methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate (1:1 salt) (25.1 g) are suspended in ethyl acetate (250 ml) and shaken with saturated aqueous sodium bicarbonate solution (250 ml) until both phases are clear. The phases are separated and the organic phase is concentrated in a rotary evaporator. The residue is dissolved in 1,4-dioxane (250 ml) and 1N sodium hydroxide solution (77.4 ml) and stirred at room temperature for 18 h. Subsequently, the pH is adjusted to 7.5 using 1N hydrochloric acid (ca. 50 ml), MIBK (240 ml) is added, then the pH is readjusted to 7.0 using 1N hydrochloric acid (ca. 15 ml). The phases are separated, and the organic phase is dried over sodium sulphate and concentrated. The residue is dissolved in ethanol (90 ml) and concentrated, then again dissolved in ethanol (90 ml) and concentrated. The solidified foam is dried at 45° C. for 18 h in the VDO using entraining nitrogen. A total of 12 g of (S)-{8-fluoro-2-[4-(3-methoxyphenyl)piperazin-1-yl]-3-(2-methoxy-5-trifluoromethylphenyl)-3,4-dihydro-quinazolin-4-yl}acetic acid are thus obtained as an amorphous solid, corresponding to 81.2% of theory.

HPLC (method 1): $R_T$=15.1 min;
HPLC (method 2): 97.5% e.e.; Pd (ICP): <20 ppm.

Alternative Process for Racemization:

Example 18

(±)-{8-Fluoro-2-[4-(3-methoxyphenyl)piperazin-1-yl]-3-(2-methoxy-5-trifluoromethylphenyl)-3,4-dihydroquinazolin-4-yl}acetic acid/hydrolysis of Concentrated R Isomer from the Mother Liquor After Crystallization The mother liquor from a crystallization of (2S,3S)-2,3-bis[(4-methylbenzoyl)oxy]succinic acid-methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate (1:1 salt) on the 207 g scale is shaken with saturated aqueous sodium bicarbonate solution (500 ml), the phases are separated and the organic phase is shaken with semi-saturated aqueous sodium bicarbonate solution (500 ml). The phases are separated, and the organic phase is dried over sodium sulphate and concentrated in a rotary evaporator. The residue is dissolved in ethanol (500 ml) and concentrated in a rotary evaporator to give a hard foam. This is dissolved in 1,4-dioxane (1.6 l) and 1N sodium hydroxide solution (1.04 l) and stirred at room temperature for 18 h, then toluene (1.5 l) is added and the phases are separated. The aqueous phase is adjusted from pH 14 to pH 8 using hydrochloric acid (20% strength, ca. 155 ml), then MIBK (1.25 l) is added and the mixture is readjusted to pH 7 using hydrochloric acid (20% strength, ca. 25 ml). The phases are separated, and the organic phase is dried over sodium sulphate and concentrated in a rotary evaporator to give a hard foam. This is dried at 45° C. for 18 h in the VDO using entraining nitrogen. A total of 150 g {8-fluoro-2-[4-(3-methoxyphenyl)piperazin-1-yl]-3-(2-methoxy-5-trifluoromethylphenyl)-3,4-dihydroquinazolin-4-yl}acetic acid are thus obtained as an amorphous solid as an (R/S) mixture.

HPLC (method 2): −14.6% e.e.

Example 19

(±)-{8-Fluoro-2-[4-(3-methoxyphenyl)piperazin-1-yl]-3-(2-methoxy-5-trifluoromethylphenyl)-3,4-dihydroquinazolin-4-yl}acetic acid/racemization {8-Fluoro-2-[4-(3-methoxyphenyl)piperazin-1-yl]-3-(2-methoxy-5-trifluoromethylphenyl)-3,4-dihydroquinazolin-4-yl}acetic acid (150 g, R/S mixture with −14.6% e.e.) is dissolved in acetonitrile (1.5 l) and treated with sodium methoxide (30% strength in methanol, 97.2 ml), then stirred under reflux for 77 h. After cooling to room temperature, the mixture is concentrated to one half in vacuo, then it is adjusted from pH 13 to pH 7.5 using hydrochloric acid (20% strength, ca. 80 ml), MIBK (0.6 l) is added and it is readjusted to pH 7 using hydrochloric acid (20% strength, ca. 3 ml). The phases are separated, and the organic phase is dried over sodium sulphate and concentrated in a rotary evaporator to give a hard foam. The residue is dissolved in ethanol (500 ml) and concentrated in a rotary evaporator, then again dissolved in ethanol (500 ml) and concentrated, then dried for 18 h at 45° C. in the VDO using entraining nitrogen. A total of 148 g of (±)-{8-fluoro-2-[4-(3-methoxyphenyl)piperazin-1-yl]-3-(2-methoxy-5-trifluoromethylphenyl)-3,4-dihydroquinazolin-4-yl}acetic acid are obtained as an amorphous solid, corresponding to 98.7% of theory.

HPLC (method 2): 1.5% e.e.

Example 20

Methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate (Esterification)

(±)-{8-Fluoro-2-[4-(3-methoxyphenyl)piperazin-1-yl]-3-(2-methoxy-5-trifluoromethylphenyl)-3,4-dihydroquinazolin-4-yl}acetic acid (148 g) is dissolved in methanol (1480 g), then concentrated sulphuric acid (21.5 ml) is added. The mixture is stirred under reflux for 6 h, then cooled and concentrated to ca. one third of the original volume in vacuo. Water (400 ml) and dichloromethane (400 ml) are added, then the phases are separated. The organic phase is extracted with saturated sodium hydrogencarbonate solution (two times 375 ml, diluted with 300 ml of water), dried over sodium sulphate and concentrated to give a foamy residue. This is dissolved twice in succession in ethanol (400 ml each) and concentrated, and subsequently dried in vacuo for 18 h using entraining nitrogen. A total of 124 g of methyl {8-fluoro-2-[4-(3-methoxyphenyl)piperazin-1-yl]-3-[2-methoxy-5-(trifluoromethyl)phenyl]-3,4-dihydroquinazolin-4-yl}acetate are thus obtained as an amorphous solid, corresponding to 81.9% of theory.

HPLC (method 1): $R_T$=16.9 min.;

Example 21

(2S,3S)-2,3-Bis[(4-methylbenzoyl)oxy]succinic acid-methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate (1:1 salt)/crystallization of Esterified Racemate (2S,3S)-2,3-Bis[(4-methylbenzoyl)oxy]succinic acid-methyl {8-fluoro-2-[4-(3-methoxyphenyl)-piperazin-1-yl]-3-[2-methoxy-5-(trifluoromethyl)phenyl]-3,4-dihydroquinazolin-4-yl}acetate (1:1 salt) (123 g, −14.4% e.e.) is suspended in ethyl acetate (861 ml) and filtered, then (2S,3S)-2,3-bis[(4-methylbenzoyl)oxy]succinic acid (82.5 g) is added. The mixture is stirred at room temperature for 30 min, then it is seeded with (2S,3S)-2,3-bis[(4-methylbenzoyl)oxy]succinic acid-methyl {8-fluoro-2-[4-(3-methoxyphenyl)piperazin-1-yl]-3-[2-methoxy-5-(trifluoromethyl)-phenyl]-3,4-dihydroquinazolin-4-yl}acetate (1:1 salt) (0.24 g). The suspension is stirred at RT for 4 days, subsequently concentrated down to ca. 600 ml and again seeded with (2S,3S)-2,3-bis[(4-methylbenzoyl)oxy]succinic acid-methyl {8-fluoro-2-[4-(3-methoxyphenyl)piperazin-1-yl]-3-[2-methoxy-5-(trifluoromethyl)phenyl]-3,4-dihydroquinazolin-4-yl}acetate (1:1 salt) (0.24 g). The suspension is stirred at RT for 1 week, cooled to 0-5° C. and stirred for a further 3 h, then the solid is filtered off with suction and washed with cold ethyl acetate (0-10° C., 4×40 ml). The crystals are dried at 45° C. for 18 h in the VDO using entraining nitrogen. A total of 11.8 g of the salt are obtained as the solid, corresponding to 5.8% of theory.

Scheme 7:

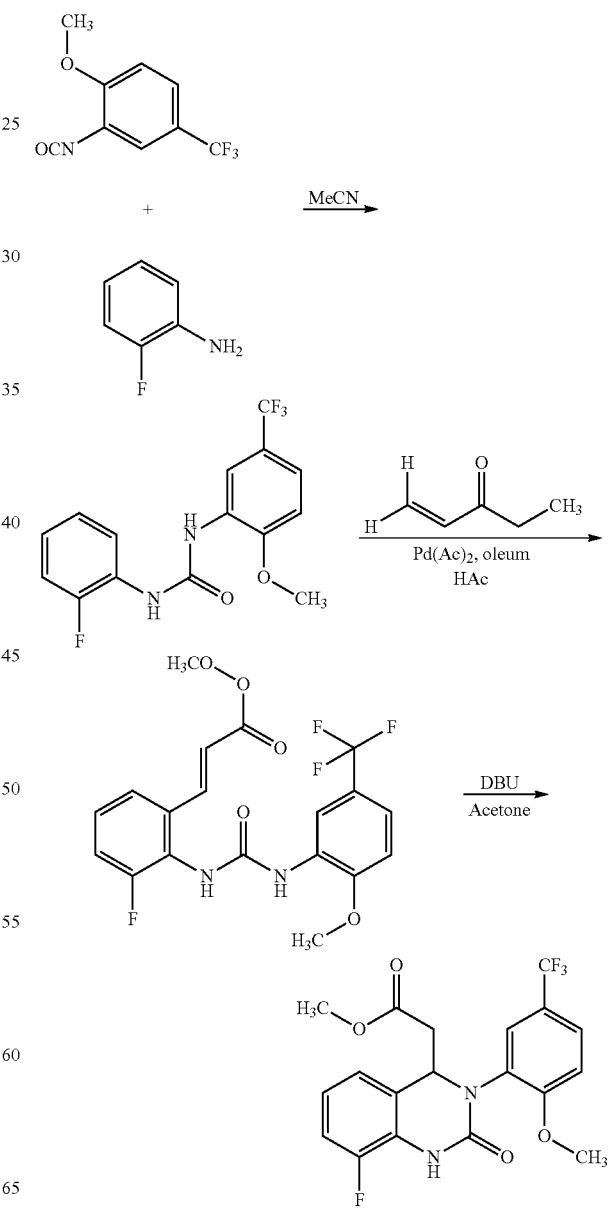

Example 22

N-(2-Fluorophenyl)-N'-[2-methoxy-5-(trifluoromethyl)phenyl]urea

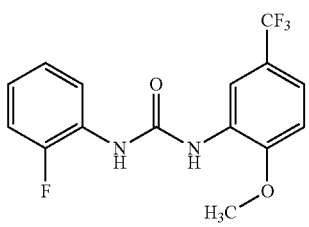 [SMILES: COc1ccc(C(F)(F)F)cc1NC(=O)Nc1ccccc1F]

2-Methoxy-5-trifluoromethylphenyl isocyanate (1057.8 g) is dissolved in acetonitrile (4240 ml), then 2-fluoroaniline (540.8 g) is added thereto and the mixture is rinsed in with acetonitrile (50 ml). The resulting clear solution is stirred under reflux (ca. 82° C.) for 4 h, then seeded at ca. 78° C. and stirred for ca. 15 min. The suspension is cooled to 0° C., and the product is filtered off with suction and washed with acetonitrile (950 ml, cooled to 0-5° C.). The product is dried overnight at 45° C. in a vacuum drying oven using entraining nitrogen. A total of 1380.8 g of N-(2-fluorophenyl)-N'-[2-methoxy-5-(trifluoromethyl)phenyl]urea are obtained as a solid, corresponding to 86.4% of theory.

$^1$H NMR (500 MHz, $d_6$-DMSO): δ=9.36 (s, 1H), 9.04 (s, 1H), 8.55 (d, 1.7 Hz, 1H), 8.17 (t, 8.2 Hz, 1H), 7.33 (d, 8.5 Hz, 1H), 7.20-7.26 (m, 2H), 7.14 (t, 7.6 Hz, 1H), 7.02 (m, 1H), 3.97 (s, 3H) ppm;

MS (API-ES-pos.): m/z=329 [(M+H)$^+$, 100%];

HPLC: $R_T$=48.7 min.

Instrument: HP 1100 with multiple wavelength detection; column: Phenomenex-Prodigy ODS (3) 100 A, 150 mm×3 mm, 3 μm; eluent A: (1.36 g of KH$_2$PO$_4$+0.7 ml of H$_3$PO$_4$)/l of water, eluent B: acetonitrile; gradient: 0 min 20% B, 40 min 45% B, 50 min 80% B, 65 min 80% B; flow: 0.5 ml/min; temp.: 55° C.; UV detection: 210 nm.

Example 23

Methyl (2E)-3-{3-fluoro-2-[({[2-methoxy-5-(trifluoromethyl)phenyl]amino}carbonyl)amino]-phenyl}acrylate

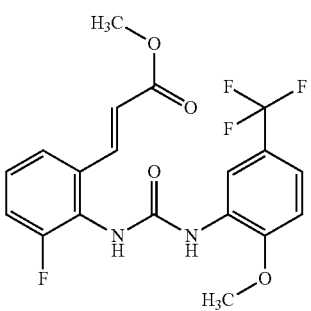 [SMILES: COC(=O)/C=C/c1cccc(F)c1NC(=O)Nc1cc(C(F)(F)F)ccc1OC]

N-(2-Fluorophenyl)-N'-[2-methoxy-5-(trifluoromethyl)phenyl]urea (0.225 kg) is dissolved in acetic acid (6.75 l) and treated with palladium acetate (30.3 g). 65% strength oleum (247.5 g) is then metered in and methyl acrylate (90 g) is subsequently added. The solution is stirred at room temperature overnight. Subsequently, acetic acid (3740 g) is distilled off at 30° C. and ca. 30 mbar. The suspension is treated with water (2.25 l) and stirred for ca. 1 hour. The product is filtered off with suction, washed twice with water (0.5 l) and dried at 50° C. overnight in the vacuum drying oven using entraining nitrogen. A total of 210.3 g of methyl (2E)-3-{3-fluoro-2-[({[2-methoxy-5-(trifluoromethyl)phenyl]amino}carbonyl) amino]phenyl}acrylate are obtained as a solid, corresponding to 72.2% of theory.

$^1$H NMR (300 MHz, $d_6$-DMSO): δ=9.16 (s, 1H), 8.84 (s, 1H), 8.45 (d, 1.7 Hz, 1H), 7.73 (m, 2H), 7.33 (m, 3H), 7.22 (d, 8.6 Hz, 1H), 6.70 (d, 16 Hz, 1H), 3.99 (s, 3H), 3.71 (s, 3H) ppm;

MS (API-ES-pos.): m/z=429.9 [(M+NH$_4$)$^+$]; 412.9 [(M+H)$^+$]

HPLC: $R_T$=46.4 min.

Instrument: HP 1100 with multiple wavelength detection; column: Phenomenex-Prodigy ODS (3) 100 A, 150 mm×3 mm, 3 μm; eluent A: (1.36 g KH$_2$PO$_4$+0.7 ml H$_3$PO$_4$)/l of water, eluent B: acetonitrile; gradient: 0 min 20% B, 40 min 45% B, 50 min 80% B, 65 min 80% B; flow: 0.5 ml/min; temp.: 55° C.; UV detection: 210 nm.

Example 24

Methyl {8-fluoro-3-[2-methoxy-5-(trifluoromethyl)phenyl]-2-oxo-1,2,3,4-tetrahydroquinazolin-4-yl}acetate

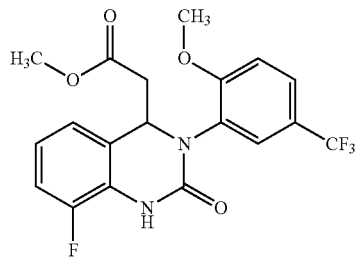

Methyl (2E)-3-{3-fluoro-2-[({[2-methoxy-5-(trifluoromethyl)phenyl]amino}carbonyl)amino]-phenyl}acrylate (50 g) is suspended in acetone (1.2 l) and treated with 1,8-diazobicyclo[5.4.0]undec-7-ene (3.7 g). The suspension is warmed to reflux (ca. 56° C.) and stirred for 4 h. The resulting clear solution is filtered warm through kieselguhr (5 g). The kieselguhr is rinsed with warm acetone (100 ml). Subsequently, acetone (550 g) is distilled off. The resulting suspension is cooled to 0° C. in the course of 3 h and stirred. The product is filtered off with suction, washed twice with cold acetone (50 ml) and dried at 45° C. overnight in the vacuum drying oven using entraining nitrogen. A total of 44.5 g of methyl {8-fluoro-3-[2-methoxy-5-(trifluoromethyl)phenyl]-2-oxo-1,2,3,4-tetrahydroquinazolin-4-yl}acetate are obtained as a solid, corresponding to 89% of theory.

$^1$H NMR (300 MHz, $d_6$-DMSO): δ=9.73 (s, 1H), 7.72 (d, $^2$J=7.3, 1H), 7.71 (s, 1H), 7.33 (d, $^2$J=9.3, 1H), 7.15 (dd, $^2$J=9.6, $^2$J=8.6, 1H), 7.01 (d, $^2$J=7.3, 1H), 6.99-6.94 (m, 1H), 5.16 (t, $^2$J=5.9, 1H), 3.84 (s, 3H), 3.41 (s, 3H), 2.81 (dd, $^2$J=15.4, $^2$J=5.8, 1H), 2.62 (dd, $^2$J=15.4, $^2$J=6.3, 1H) ppm;

MS (API-ES-pos.): m/z=413 [(M+H)$^+$, 100%], 825 [(2M+H)$^+$, 14%];

HPLC: $R_T$=37.1 min.

Instrument: HP 1100 with multiple wavelength detection; column: Phenomenex-Prodigy ODS (3) 100 A, 150 mm×3 mm, 3 μm; eluent A: (1.36 g of $KH_2PO_4$+0.7 ml of $H_3PO_4$)/l of water, eluent B: acetonitrile; gradient: 0 min 20% B, 40 min 45% B, 50 min 80% B, 65 min 80% B; flow: 0.5 ml/min; temp.: 55° C.; UV detection: 210 nm.

The invention claimed is:

1. A process for isolating methyl (S)-{8-fluoro-2-[4-(3-methoxyphenyl)piperazin-1-yl]-3-[2-methoxy-5-(trifluoromethyl)phenyl]-3,4-dihydroquinazolin-4-yl}acetate (2S,3S)-2,3-bis[(4-methylbenzoyl)-oxy]succinic acid salt, comprising crystallizing racemic methyl-{8-fluoro-2-[4-(3-methoxyphenyl)piperazin-1-yl]-3-[2-methoxy-5-(trifluoromethyl)phenyl]-3,4-dihydroquinazolin-4-yl}acetate with (2S,3S)-2,3-bis[(4-methylbenzoyl)oxy]succinic acid.

2. Methyl (S)-{8-fluoro-2-[4-(3-methoxyphenyl)piperazin-1-yl]-3-[2-methoxy-5-(trifluoro-methyl)-phenyl]-3,4-dihydroquinazolin-4-yl}acetate (2S,3S)-2,3-bis[(4-methylbenzoyl)-oxy]succinic acid salt.

* * * * *